US010369027B2

(12) United States Patent
Alley

(10) Patent No.: US 10,369,027 B2
(45) Date of Patent: Aug. 6, 2019

(54) ADAPTABLE SOCKET SYSTEM, METHOD, AND KIT

(71) Applicant: Randall D. Alley, Thousand Oaks, CA (US)

(72) Inventor: Randall D. Alley, Thousand Oaks, CA (US)

(73) Assignee: Randall D. Alley, Thousand Oaks, CA (US)

( * ) Notice: Subject to any disclaimer, the term of this patent is extended or adjusted under 35 U.S.C. 154(b) by 16 days.

(21) Appl. No.: 15/012,852

(22) Filed: Feb. 2, 2016

(65) Prior Publication Data
US 2016/0158035 A1 Jun. 9, 2016

Related U.S. Application Data

(63) Continuation of application No. 13/797,957, filed on Mar. 12, 2013, now Pat. No. 9,283,093.
(Continued)

(51) Int. Cl.
A61F 2/50 (2006.01)
A61F 2/70 (2006.01)
(Continued)

(52) U.S. Cl.
CPC ............... A61F 2/78 (2013.01); A61F 2/70 (2013.01); A61F 2/76 (2013.01); A61F 2/80 (2013.01);
(Continued)

(58) Field of Classification Search
CPC ...... A61F 2/54; A61F 2/60; A61F 2/76; A61F 2/78; A61F 2/7812; A61F 2/7843;
(Continued)

(56) References Cited

U.S. PATENT DOCUMENTS 1,144,681 A 6/1915 Apgar
1,272,179 A 7/1918 Anderson
(Continued)

FOREIGN PATENT DOCUMENTS

FR 2539616 A1 7/1984
FR 2828093 A1 2/2007
GB 127451 A1 6/1918

OTHER PUBLICATIONS

Gleave. A Plastic Socket and Stump Casting Technique for Above-Knee Prostheses. Feb. 1965. Journal of Bone and Joint Surgery. Figures 1-3.
(Continued)

Primary Examiner — Thomas Sweet
Assistant Examiner — Christie L Bahena
(74) Attorney, Agent, or Firm — Fish IP Law, LLP

(57) ABSTRACT

An adjustable socket system, method, and kit for use with prosthetic devices or orthotic, orthopedic, or exoskeletal support devices that includes a paddle and a compressing device coupled to the paddle. The paddle is chosen from a plurality of paddles of different shapes in such a way that the paddle inner surface is substantially coextensive with a soft tissue area overlying skeletal structures. The compressing device presses the paddle against the soft tissue area in order to minimize the motion of the paddle relative to the underlying skeletal structures without causing discomfort to the user or compressing areas not in contact with the paddle, allowing compressed tissue to flow into uncompressed areas. The system, method, and kit can include an external tool, sensors, actuators, and controllers, to assist fitting and for adjustment after fitting. A stabilizer can be added to resist the bending force on the paddle.

16 Claims, 25 Drawing Sheets

Related U.S. Application Data

(60) Provisional application No. 61/732,493, filed on Dec. 3, 2012, provisional application No. 61/720,934, filed on Oct. 31, 2012.

(51) Int. Cl.

| | | |
|---|---|---|
| *A61F 2/76* | (2006.01) | |
| *A61F 2/78* | (2006.01) | |
| *A61F 5/01* | (2006.01) | |
| *A61F 2/80* | (2006.01) | |

(52) U.S. Cl.
CPC ...... *A61F 5/0102* (2013.01); *A61F 2002/509* (2013.01); *A61F 2002/5016* (2013.01); *A61F 2002/5026* (2013.01); *A61F 2002/5027* (2013.01); *A61F 2002/5052* (2013.01); *A61F 2002/5083* (2013.01); *A61F 2002/764* (2013.01); *A61F 2002/7635* (2013.01); *A61F 2002/7675* (2013.01); *A61F 2002/802* (2013.01)

(58) Field of Classification Search
CPC ...... A61F 2002/5016; A61F 2002/5026; A61F 2002/5083; A61F 2002/509; A61F 2002/5027; A61F 2002/5052

See application file for complete search history.

(56) References Cited

U.S. PATENT DOCUMENTS

| | | | |
|---|---|---|---|
| 2,229,728 | A | 1/1941 | Eddels |
| 2,506,464 | A | 5/1950 | Millheisler |
| 2,658,388 | A | 11/1953 | Feine |
| 3,111,683 | A | 11/1963 | Bach |
| 4,128,903 | A | 12/1978 | Marsh et al. |
| 4,459,709 | A | 7/1984 | Leal |
| 5,003,969 | A | 4/1991 | Azer et al. |
| 5,246,464 | A | 9/1993 | Sabolich |
| 5,288,286 | A | 2/1994 | Davis |
| 5,405,405 | A | 4/1995 | Love |
| 5,458,599 | A | 10/1995 | Adobbati |
| 5,507,836 | A | 4/1996 | Pohlig |
| 5,724,714 | A | 3/1998 | Love |
| 5,888,230 | A | 3/1999 | Helmy |
| 6,077,300 | A | 6/2000 | Sabolich et al. |
| 6,482,238 | B1 | 11/2002 | Grundei |
| 6,991,657 | B1 | 1/2006 | Price, Jr. |
| 6,994,732 | B2 | 2/2006 | Steinbarger et al. |
| 7,377,944 | B2 | 5/2008 | Janusson |
| 7,817,004 | B2 | 10/2010 | Fullerton et al. |
| 8,241,296 | B2 | 8/2012 | Wasielewski |
| 8,298,293 | B2 | 10/2012 | Leydet |
| 8,323,353 | B1 | 12/2012 | Alley et al. |
| 8,409,298 | B2 | 4/2013 | Perkins |
| 8,443,501 | B2 | 5/2013 | Mahon |
| 8,656,918 | B1 | 2/2014 | Alley et al. |
| 9,283,093 | B2 | 3/2016 | Alley |
| 2002/0193887 | A1 | 12/2002 | Swanson, Sr. |
| 2003/0195636 | A1 | 10/2003 | Coop |
| 2004/0158332 | A1 | 8/2004 | Carstens |
| 2008/0147204 | A1 | 6/2008 | Ezenwa |
| 2008/0161938 | A1 | 7/2008 | Gramnas |
| 2010/0042227 | A1 | 2/2010 | Schmidt |
| 2010/0082116 | A1 | 4/2010 | Johnson et al. |
| 2010/0274364 | A1 | 10/2010 | Pacanowsky et al. |
| 2011/0247321 | A1 | 10/2011 | Streeter et al. |
| 2012/0101597 | A1 | 4/2012 | Bache |
| 2012/0271433 | A1 | 10/2012 | Galea et al. |
| 2013/0053981 | A1 | 2/2013 | Alley |
| 2013/0123940 | A1 | 5/2013 | Hurley |
| 2014/0005798 | A1 | 1/2014 | Bache |
| 2014/0135946 | A1 | 5/2014 | Hurley et al. |
| 2017/0065442 | A1 | 3/2017 | Alley |
| 2017/0156896 | A1 | 6/2017 | Alley |

OTHER PUBLICATIONS

Bennett. Recent Advances in Above-Knee Prosthetics. Artificial Limbs. 1968. vol. 12, No. 2 pp. 1-27. Figure 5.
Jalleytwo. High-Fidelity Prosthetic Socket. Post date: Jun. 10, 2011. http://www.youtube.com/watch?v=NBNV7d46rQ4.
Ohio Willow Wood Liners. http://www.willowwoodco.com/products-and-services/liners Verified by the wayback machine Mar. 26, 2011.
Davis, Scott. Young Afghan amputee gets new arms. The United States Army. Mar. 28, 2011.
Krouskop, Dougherty. Measuring the shape and volume of an above-knee stump. Prosthetics and Orthotics International. 1988, 12, 136-142.
ISA/KR, Notification of Transmittal of the International Search Report and the Written Opinion of the International Searching Authority, or the Declaration, dated Feb. 6, 2014, PCT/US2013/067085.
ISA/KR, Written Opinion of the International Searching Authority, dated Feb. 6, 2014, PCT/US2013/067085.
ISA/KR, International Search Report, dated Feb. 6, 2014, PCT/US2013/067085.
Randall D Alley, "Prosthetic sockets stabilized by alternating areas of tissue compression and release," Journal of Rehabilitation Research & Development, vol. 48 No. 6, 2011, pp. 679-696.
"Biodesigns Inc Maximizing Human Performance", advertisement, inMotion Magazine, Apr. 2008 (1 page).
Randall Alley, "New Interface Design Benefits the High Performance Individual", article, Challenge Magazine, Jun. 2008 (1 page).
"RCR Transtibial Socket", web page from www.coyotedesign.com, printed Dec. 11, 2009 (1 pg.).
Pre-Brief Appeal Conference decision dated Mar. 22, 2016, U.S. Appl. No. 13/663,282.
Examiner's Answer dated Sep. 23, 201, U.S. Appl. No. 13/663,282.
PI01091EP1 Extended European Search Report, dated Aug. 1, 2016.
Charles G. Hater, MD, "A Suction Socket Prosthesis Without Suction," article, Orthopedic & Prosthetic Appliance Journal, Sep. 1957 (5 pages).
R. Volkert, "Frame type socket for lower limb prostheses," article, Prosthetics and Orthotics International, 1982, 6, 88-92.
Decision on Appeal, dated Mar. 21, 2017, U.S. Appl. No. 12/663,282.
Alley, U.S. Appl. No. 15/258,727, filed Feb. 23, 2017.
Decision on Request for Rehearing, dated Jun. 2, 2017, U.S. Appl. No. 13/663,282.
Office Action dated Aug. 11, 2017, U.S. Appl. No. 14/156,962.
ISA/KR, Notification of Transmittal of the International Search Report and the Written Opinion of the International Searching Authority, or the Declaration, dated Jun. 15, 2016, PCT/US2016/017178.
ISA/KR, Written Opinion of the International Searching Authority, dated Jun. 15, 2016, PCT/US2016/017178.
ISA/KR, International Search Report, dated Jun. 15, 2016, PCT/US2016/017178.
Alley, U.S. Appl. No. 15/258,727, filed Sep. 7, 2016.

ADAPTABLE SOCKET SYSTEM, METHOD, AND KIT

CROSS REFERENCE TO RELATED APPLICATIONS

This application claims the benefit of priority from U.S. Nonprovisional application Ser. No. 13/797,957, filed Mar. 12, 2013; U.S. Provisional Patent Application No. 61/732,493, filed Dec. 3, 2012; and U.S. Provisional Patent Application No. 61/720,934, filed Oct. 31, 2012, all of which applications are incorporated in their entirety by reference herein.

FIELD OF THE INVENTION

The present invention relates to the prosthetic limbs worn by upper or lower limb human or animal amputees and in particular, to the portions of limb prostheses that are in direct contact with the user's limb. It also relates to orthotic support devices applied and worn to support or supplement weakened or abnormal joints or limbs. It also relates to immobilizing injured skeletal structures and associated muscles, joints, and ligaments, for example, using orthopedic support devices in the field of orthopedics. Finally, it relates to the human or animal interface component of exoskeletal support devices and associated machines, or systems.

BACKGROUND OF THE INVENTION

A conventional prosthesis socket is generally circular in cross section and consists of an inner socket to interface with the user's skin and an outer socket over it that incorporates the mechanisms that comprise an additional structure, for example, an artificial joint or a device to function as a foot or gripping device. The inner and outer sockets may be separate structures or may consist of a single unit.

The term "interface" is used by some in the field as a synonym for socket, but in this disclosure the term "socket" is used exclusively.

The term "cast" conventionally refers to a thin layer of wet plaster impregnated gauze wrapped around a residual limb and the surrounding body parts and then permitted to harden to reproduce the shape of the limb. While the plaster is hardening, pressure from the hands of the plaster technician often modifies the shape to accommodate the underlying boney anatomy.

The term "positive model" refers to the plaster model that results from filling a cast with plaster or similar material. Modifications by adding and subtracting plaster are made to the positive model before its outer surface is used to define the shape of the user's socket.

The term "check socket" is a temporary socket made using the positive model and used to test whether the modifications have had the desired effect on the fit of the resulting socket.

Historically the socket for prosthetic applications has been a generally cylindrical socket that merely surrounds the remaining limb part with some contouring of the proximal brim so that it will accommodate the shape of the next proximal joint or body part. Typically, this socket is made by taking a plaster cast over the limb and filling it with plaster to form a positive model of the limb. Minor changes are made to this shape to conform to boney prominences. When the positive model is used to create a socket by laminating or thermoforming a layer of plastic over the model, the resulting socket primarily encapsulates the limb part.

Some improvements have been made in the conventional socket. In particular, many technicians replace the fully encapsulating outer socket with a frame having one or more openings. This change is accompanied by making the inner socket of a flexible material. The resulting frame-style design usually is more comfortable. New materials such as carbon fiber composites add rigidity where needed especially in open frame designs. New flexible materials allow the socket wall to flex in some areas for comfort. Even when these newer flexible materials are used, the soft liner still fully encapsulates the remaining limb as conventionally done and, thus, provides a compressive or elastic force to all of the limb's soft tissue.

Conventional laminations over a positive model work best when the surfaces of the positive model are convex facing outward, following the general contours of the outside surface of the limb.

Fitting a conventional socket is a multistage process involving creating a cast, waiting for it to dry, making a positive model of the initial cast, waiting for it to dry, creating a test socket, waiting for it to dry, adjusting the positive model, and then finally creating the final socket. To tailor further the fit to the patient, the castings removed from each mold usually must be further shaped, often by hand, to achieve the comfort and wearability required by the user.

Thus, the user of these conventional sockets is faced with the disadvantage of spending an extensive period of time being fit with the socket, and may need to visit the offices of the socket designer several times over the course of having the socket fit. A secondary disadvantage of this conventional method of making the socket is its expense due to the need for a skilled professional to handcraft the socket during the time intensive fitting process.

SUMMARY OF THE INVENTION

An overlooked disadvantage of conventional sockets is the lost motion between the socket walls and the underlying skeletal structures when force is applied between the two as would occur as an amputee tries to move the prosthesis as a whole. In a conventional socket, lost motion occurs when the bone moves towards the socket wall a substantial distance before imparting force to the wall. The conventional socket merely contains the soft tissue but does little or nothing to prevent lost motion between the socket and the underlying skeletal structure. Thus, users of these conventional sockets are left with no choice but to accept a degree of disassociation between the physical movements of the body part in the socket and the resulting movement of the socket and attached prosthetic. The fields of orthotics, orthopedics, and exoskeletal support devices similarly have overlooked this disadvantage. In the case of orthotics or orthopedics, this disadvantage can lead to re-injury, poorer correction, or longer periods for successful rehabilitation.

The concept of capturing the lost motion through skeletal compression and tissue displacement can be understood from a simple observation using a procedure such as described in this paragraph. A person (the "subject") holds her arm in a fixed position so that an observer cannot easily move the arm side to side. The observer then pushes with a finger on the fleshy area over the long bone of the upper arm. During compression, tissue moves aside, away from the area of compression. Typically, the finger will push into the soft tissue a distance of a centimeter or more before it compresses the tissue against the bone and no further motion is possible without the subject moving. The reverse is also true. If the finger is held steady, just touching the fleshy area, and the subject pushes her arm against the finger, the finger will push into the soft tissue the same distance before the arm stops because the finger has compressed the tissue against the bone as in the first example. This distance the arm travels towards the finger before the arm stops represents the lost motion. Once the arm has stopped, the lost motion has been captured in accordance with the principles of the invention and no additional motion will be lost if the subject continues to move his or her arm against the finger.

It is also to be appreciated that the cross sectional dimension of the subject's arm at the point of compression over underlying bone will be less in the direction of the compression than it was prior to the compression (when the arm was "at rest"). Conversely, the cross sectional dimension of the arm adjacent to the point of compression will be larger in the direction of the compression than it was prior to compression. In each case, this is because the tissue flows away from the compression and bulges up against adjacent tissue in the same manner water flows away from a compressive force and against adjacent water creating a wave crest that is taller than the pre-compression, "at rest" water level. Thus, it is a principle of the lost motion capture concept that, unless constrained, the cross sectional dimensions of a body part subjected to compression over underlying bone will be reduced and increased through skeletal compression and tissue displacement relative to the at rest cross sectional dimensions of the body part.

In accordance with the principles of the invention, an adjustable socket system, method, and kit, (collectively referred to herein as "the Rapidly Adaptable Socket System" or "RAS System") solves the problem of lost motion between the skeletal structure and socket walls and the expensive and time consuming fitting process by combining a compressing device which itself is also a fitting tool with paddles that displace excess tissue, capture underlying skeletal structures using optimal tissue compression selectable to ensure wearability, and permits the user to simply wear the fitting tool and paddles as the new socket when the fitting process is complete. Additional embodiments of the invention enhance the solution by allowing manual or automatic post-fitting adjustments so that changes in the user's body mass, tissue volume, or activity level, or fitting corrections can be made by the user or socket designer without reiterating the conventional fitting process. Finally, further embodiment variations solve the fitting and adaption process problem by mounting electronics on the RAS, or external fitting tools, or both, which allow monitoring, recording, or controlling the RAS fit in accordance with the principles of the invention The following terms have the following meanings in this disclosure:

The term "relief area" describes the region in the RAS adjacent to one or more paddles where displaced tissue is released after it flows from the area compressed by such paddles.

The term "paddle" describes the bar used to compress the skeletal structure of the target.

The term "optimal tissue compression" describes the compression force of the RAS paddles against soft tissue overlying skeletal structure such that lost motion between the RAS and the underlying skeletal structures is minimized without causing discomfort to the user for a usable amount of time.

The term "usable amount of time" describes the amount of time the RAS designer or user expects to wear the socket on a typical day or for a planned activity.

The term "target" refers to the remaining limb of an amputee, an area requiring orthotic rehabilitation or support, an injured area requiring immobilization, or a part of the body fitted with an exoskeletal support device.

The term "target area" is synonymous with "areas of compression" and refers to the area of the target selected by the socket designer for RAS paddles as, for example, disclosed in U.S. Pat. No. 8,323,353, which is incorporated herein in its entirety by this reference.

The term "nonpaddle area" describes the area of the target that is not a target area.

Embodiments of the RAS include an adapter attached to one or more compression paddles through paddle connectors. The compression paddles extend away from the adapter in the direction of the target, forming a bowl, cup, or box shaped container configuration where the adapter is at the bottom of the container and the paddles and relief area between the paddles alternate along the sides or walls of the container with the flat surfaces of the paddles generally flush with the inner surface of such container walls. The container forms a receptacle or open cage that can receive and compress the target's skeletal structure by moving the paddles inwardly towards the center of the container in accordance with the principles of the invention.

In one embodiment, the socket designer selects each paddle from a plurality of paddles of different shapes, including different widths, lengths, thicknesses, and curvatures. For example, a socket designer may check to see if a particular paddle selection rocks end-to-end when pressure is shifted, in which case the socket designer would choose a different shaped paddle that does not rock end-to-end. In a variation of this embodiment, the plurality of paddles may be premanufactured and sold in a kit along with an adapter. In still another embodiment, the socket designer may manufacture paddles as needed and keep available his own inventory of preconfigured paddle shapes to fit a variety of user.

In a preferred embodiment, the paddle lengths are selected so that they run virtually the entire length of the bone in the target, ending just short of the bone ends, however, shorter paddle lengths can be selected in particular applications. When compressed, the inner surfaces of the paddles compress the target's tissue against the bone to impart optimal tissue compression.

In a preferred embodiment where the length of the bone in the target is substantially shorter than the length of the body part overlying the bone, the paddle lengths are selected so that they run beyond the length of the bone in the target in order to apply compression to tissue beyond the bone ends to supplement the association between the physical movement of the bone and the resulting movement of the paddles by also capturing the motion of the tissue beyond the bone ends. In this embodiment, the optimal tissue compression also describes this supplemental compression force on the RAS paddles against the soft tissue beyond the bone ends.

Embodiments of the RAS include immovable paddles, once they are adjusted for the target, or adjustable paddles that the socket designer or the user can move inwards or outwards from the container center to increase or decrease compression, respectively, in order to, for example, fine tune the compression, adjust for changes in body mass or volume, or adjust for variations in the optimal tissue compression for different activities.

In some embodiments, the compression can be achieved using manual compression. In other embodiments, actuators and a controller are used to compress the paddles. In both the manual or automatic compression embodiments, feedback from sensors that detect pre-programmed paddle positions, real-time activity levels, pressure levels, physiological conditions of the target, or combinations of such feedback, allow for manual or automatic optimization and adjustment to the compression.

In some embodiments, the RAS is part of a system that includes an external positioning tool, which can include the tool's own sensors and electronics, for positioning paddles and achieving optimal tissue compression. The RAS system may also include customizable shims mounted on the paddles to achieve a better fit with the target.

Other embodiments include stabilizers or a stabilizer ring to counteract the bending force on paddles at a distance away from the adapter. In some embodiments, a membrane serves as a location to mount sensors and other electronics for monitoring and controlling compression, or to increase friction between the target and the RAS to enhance stabilization, control, and suspension of the RAS by reducing vertical, rotational, and translational motion of the target within the RAS during all phases of the gait cycle and while, for example, the user is standing or sitting.

In another embodiment, the adapter is omitted and one or more ring stabilizers maintain the relative position of the paddles around the container.

In orthotic or orthopedic embodiments of the RAS, the paddles are especially configured to interface with different parts of the body to correct or stabilize these body parts. In exoskeletal embodiments of the RAS, the paddles are especially configured to interface with different body parts to provide attachments points for desired exoskeletal applications.

In some embodiment of the RAS System, the user wears a liner between the target and the RAS to increase friction and interconnection between the target and the RAS to enhance stabilization, control, and suspension by reducing vertical, rotational, and translational motion of the target within the RAS and to support and contain soft tissue such that under weight-bearing or non-weight-bearing conditions the target is comfortably supported and contained during all phases of the gait cycle or, for example, while the user is standing, sitting, or lying down. In other embodiments, the liner incorporates one or more rings or patches of semi-flexible material to increase soft tissue support and containment in regions selected by the socket designer.

Some embodiments of the liner, fully encapsulate the target as conventionally done, and thus provide a compressive or elastic force to all of the limb's soft tissue in order to minimize edema.

In variations of the embodiments, the RAS system includes transducer (e.g., accelerometer, strain gauge, slip detector, pressure sensor, oximeter, angle position sensor, or actuator), processor, amplifier, input/output devices, or memory devices, and a power source for sensing, recording, transmitting, or controlling adapter, membrane, paddle, or stabilizer position, orientation, and relative motion, and physiological parameters of the target (for example, temperature or blood oxygen levels). Some RAS system embodiments are integrated with a computer, which can be a smart phone device, so that the user or socket designer can control or monitor the RAS through a wired or wireless communication link to the computer.

While the embodiments disclosed above have application in the field of prosthetics, in orthotic or orthopedic embodiments, the lost motion capture and adjustability principles of the invention are applied using RAS paddles to control motion of bone across a fracture or bones sharing a common joint to immobilize such fractures or joints or support joints in order to promote healing or correction, while allowing compression forces to be varied over time for therapeutic benefit, comfort, or for particular activities that may require more or less immobilization or support.

The principals of the invention are also applied in exoskeletal embodiments where the user is, for example, not an amputee, but requires a socket device that captures lost motion of the underlying skeletal structure to which the socket attaches in order, for example, to immobilize a joint, increase the load bearing strength of skeletal structures, or increase the association between the physical movement of the skeletal structure and the resulting movement of the RAS. A further advantage of the RAS system in exoskeletal applications is that it allows user adjustments in the field and the RAS can be adjusted to fit different users who may need to use the exoskeletal application at different times.

DETAILED DESCRIPTION

Figure 1:
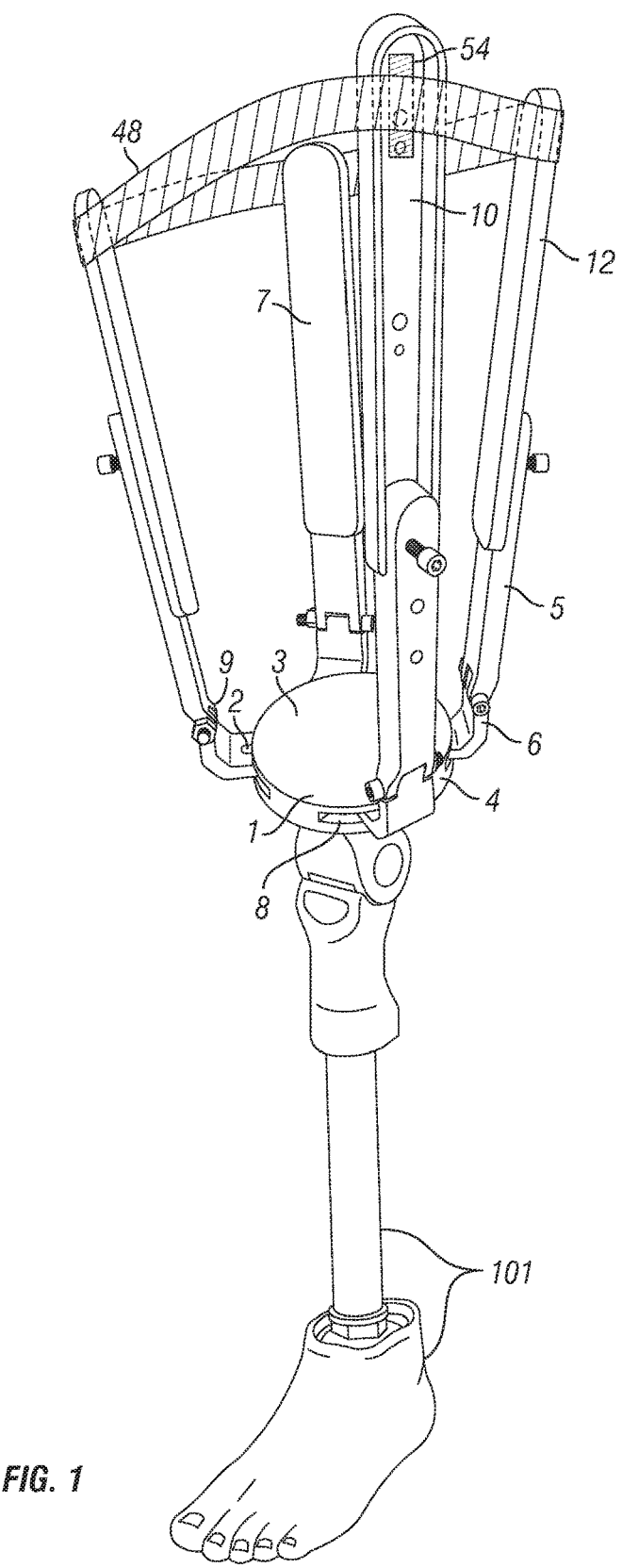
FIG. 1 is a perspective view of a RAS with a stabilizer, paddle connectors, paddles, rotatable connectors, and a prosthetic device.

FIG. 1 depicts one embodiment that includes a prosthetic device 101 and the attached RAS compressing device and paddles. The RAS compressing device and paddles include an adapter 1 with attachment points 2 arranged azimuthally around the adapter such that the attachments are aligned at distinct intervals around the circumference of the adapter, wherein the locations of these attachment points are determined with reference to the skeletal structure of the target area, as well as by the shape and size of the target. In one variation, the adapter has four attachment points. When the target is a human limb having a skeletal structure lying within the limb these attachment points are, for example, approximately ninety degrees apart.

The adapter 1 has an inner adapter surface 3 facing the target, an outer adapter surface (not shown) opposite the inner adapter surface, and side 4 connecting the inner adapter surface to the outer adapter surface.

In one variation of this embodiment, the inner adapter surface 3 is circular or ovoid.

The attachment points 2 are connectable to compression paddles 5 through paddle connectors 6.

The compression paddles 5, when attached to the adapter 1 though the paddle connectors 6, extend away from the inner adapter surface 3 of the adapter in the direction of the target, forming a bowl, cup, or box shaped container configuration where the inner adapter surface is at the bottom of the container and the paddles and relief areas between the paddles alternate along the sides or walls of the container with the flat inner surfaces of the paddles 7 generally flush with the inner surface of such container walls. The container forms a receptacle or open cage that can receive and compress the target's skeletal structure by moving the paddles inwardly towards the center of the container in accordance with the principles of the invention.

While in this embodiment the paddles 5 have substantially the same shape, more generally, the socket designer selects each paddle from a plurality of paddles of different shapes, including different widths, lengths, thicknesses, and curvatures. For example, a socket designer may check to see if a particular paddle selection rocks end-to-end when pressure is shifted, in which case the socket designer would choose a different shaped paddle that does not rock end-to-end. In a variation of the embodiment depicted, the plurality of paddles may be premanufactured and sold in a kit along with an adapter. In another embodiment, the socket designer may manufacture paddles as needed and keep available his own inventory of preconfigured paddle shapes to fit a variety of user.

In the embodiment depicted in FIG. 1, the paddle 5 lengths are selected so that they run virtually the entire length of the bone in the target, ending just short of the bone ends, e.g. along eighty and more preferably at least ninety percent of the bone length, however, shorter paddle lengths can be selected in particular applications without departing from the spirit and scope of the invention. When compressed, the inner surfaces 7 of the paddles compress the target's tissue against the bone to impart optimal tissue compression.

In one embodiment, the paddles 5, paddle connectors 6, and adapter 1 are constructed of aluminum, but other materials, including fiberglass, carbon fiber composite, plastic, or electroactive polymer material may be used and still be within the spirit and scope of the invention.

The paddle connectors 6 attach to the attachment points 2 on the adapter 1. The attachments points are located, for example on the inner adapter surface 3. However, the attachment points can also be located on the outer adapter surface or along the sides of the adapter 4. In the embodiment depicted in FIG. 1 the attachment points are located on the sides of the adapter and the paddle connectors pass through attachment openings 8 on the adapter sides. In an alternative embodiment, the inner adapter surface is recessed at such side attachment points, exposing the attachment point within the recessed area.

Figure 12:
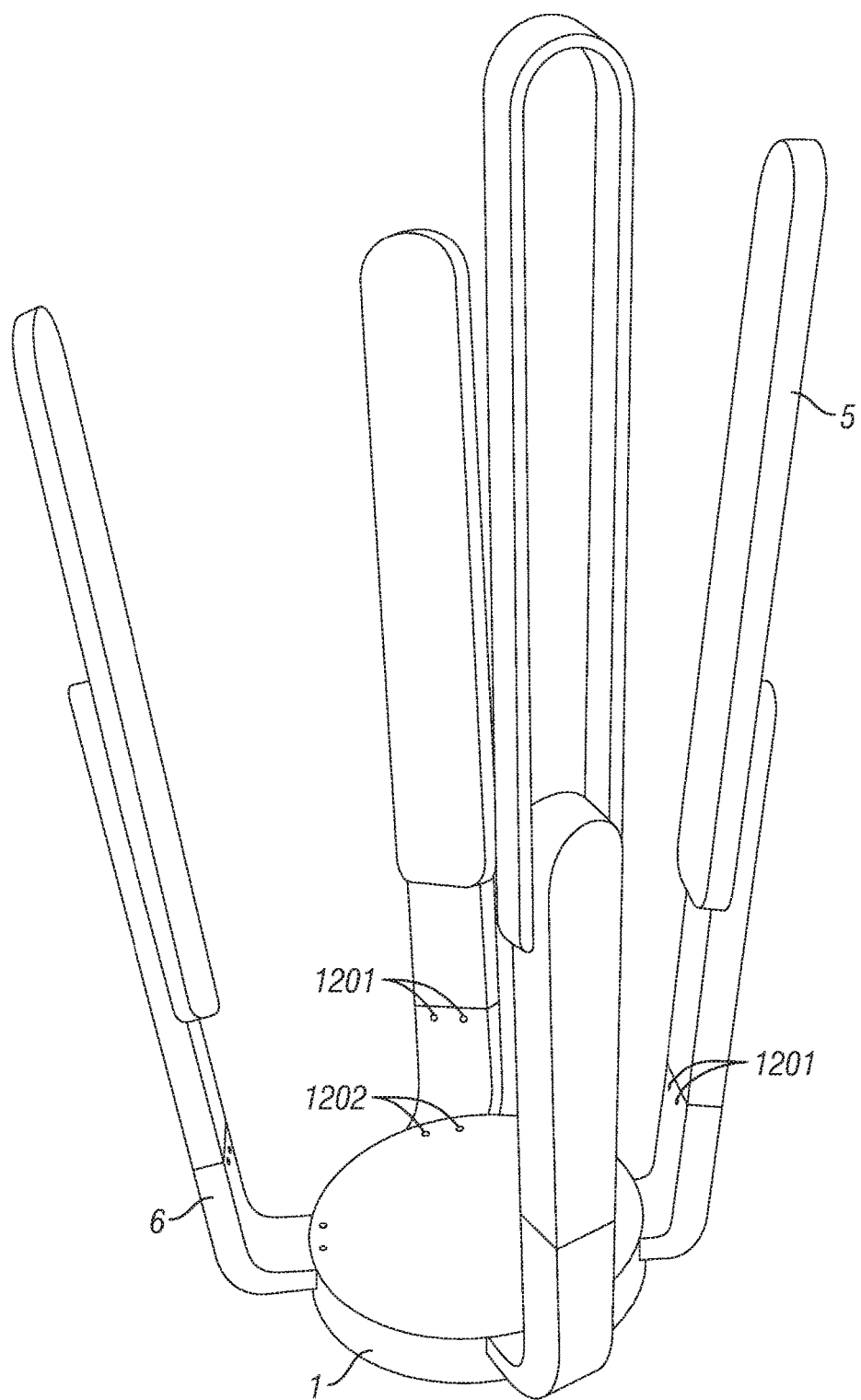
FIG. 12 is a perspective view of a RAS with paddle connectors, paddles, and an adapter connected using locking pins.

FIG. 12 depicts one embodiment where, after being adjusted to achieve optimal tissue compression, the paddles 5 are rigidly affixed to the paddle connectors 6 using paddle locking pins 1201 and the paddle connectors are rigidly affixed to the adapter 1 using connector locking pins 1202 so that the paddles are immovable relative to the adapter.

In FIG. 1, after being adjusted for an initial optimal tissue compression, the paddles 5 can be adjusted to move inwards or outwards from the container center to increase or decrease compression, respectively, in order to fine tune the compression or to adjust for changes in body mass, tissue volume, or for variations in the optimal tissue compression for different activities. In this embodiment, the paddles tilt inward or outward from the container center using a rotatable connector 9 between and coupled to the paddle connector 6 and the paddle.

Figure 13:
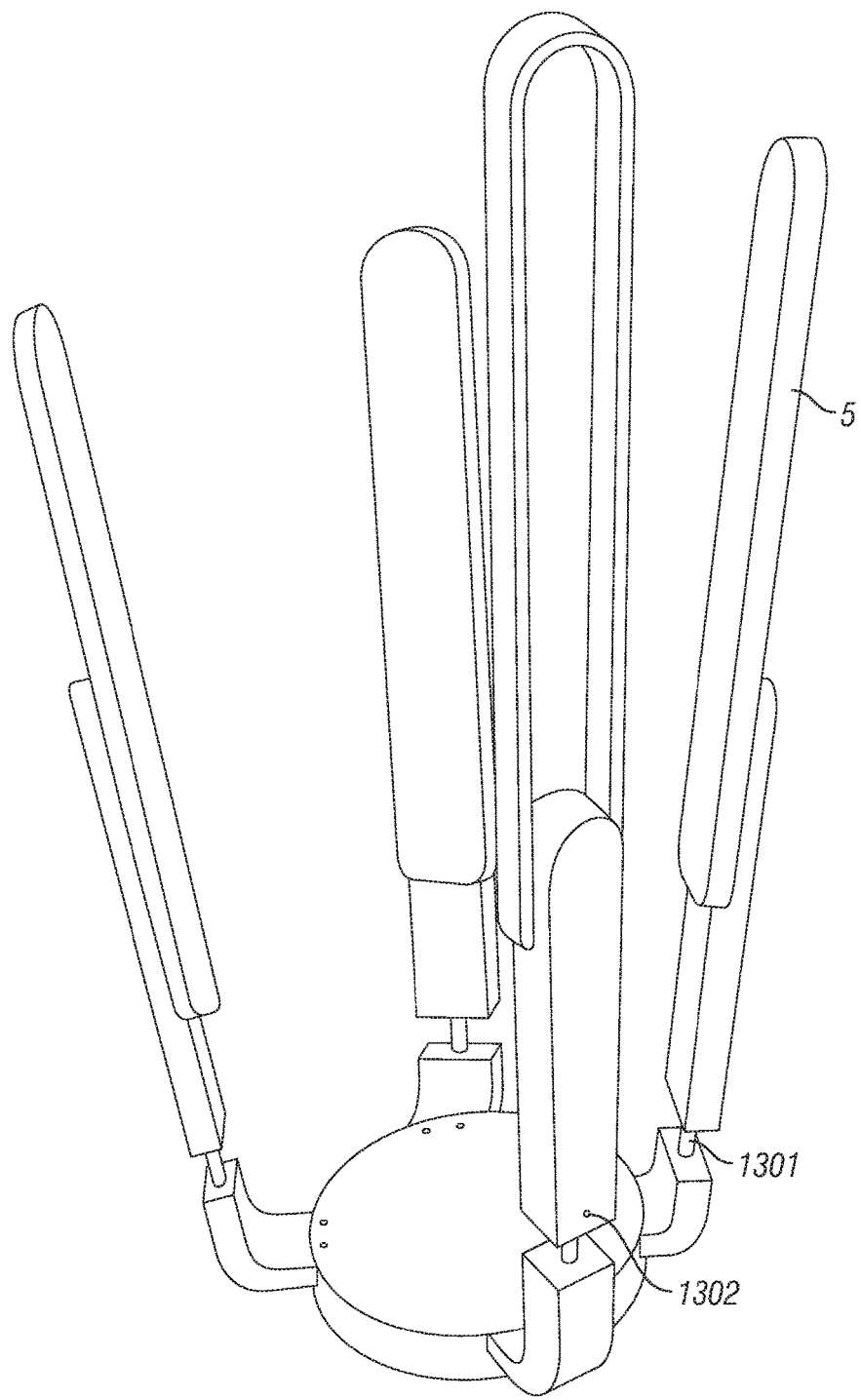
FIG. 13 is a perspective view of a RAS with paddles and paddle posts.

In another variation, depicted in FIG. 13, the paddles 5 can also rotate around their long axis to achieve optimal tissue compression adjustment by rotating about the paddle posts 1301. After adjustment, the user can lock the paddles into place with setscrews 1302. In another variation, depicted in FIG. 1, paddle connectors 6 can slide along the sides of the adapter to change the position of the associated paddles along the virtual walls of the container.

In FIG. 1, the motion can be restricted such that the paddles 5 and paddle connectors 6 can be locked in any position along their motion paths, for example, by using a setscrew (not shown) on the rotatable connector 9 between the paddle connector and the paddle.

Figure 14:
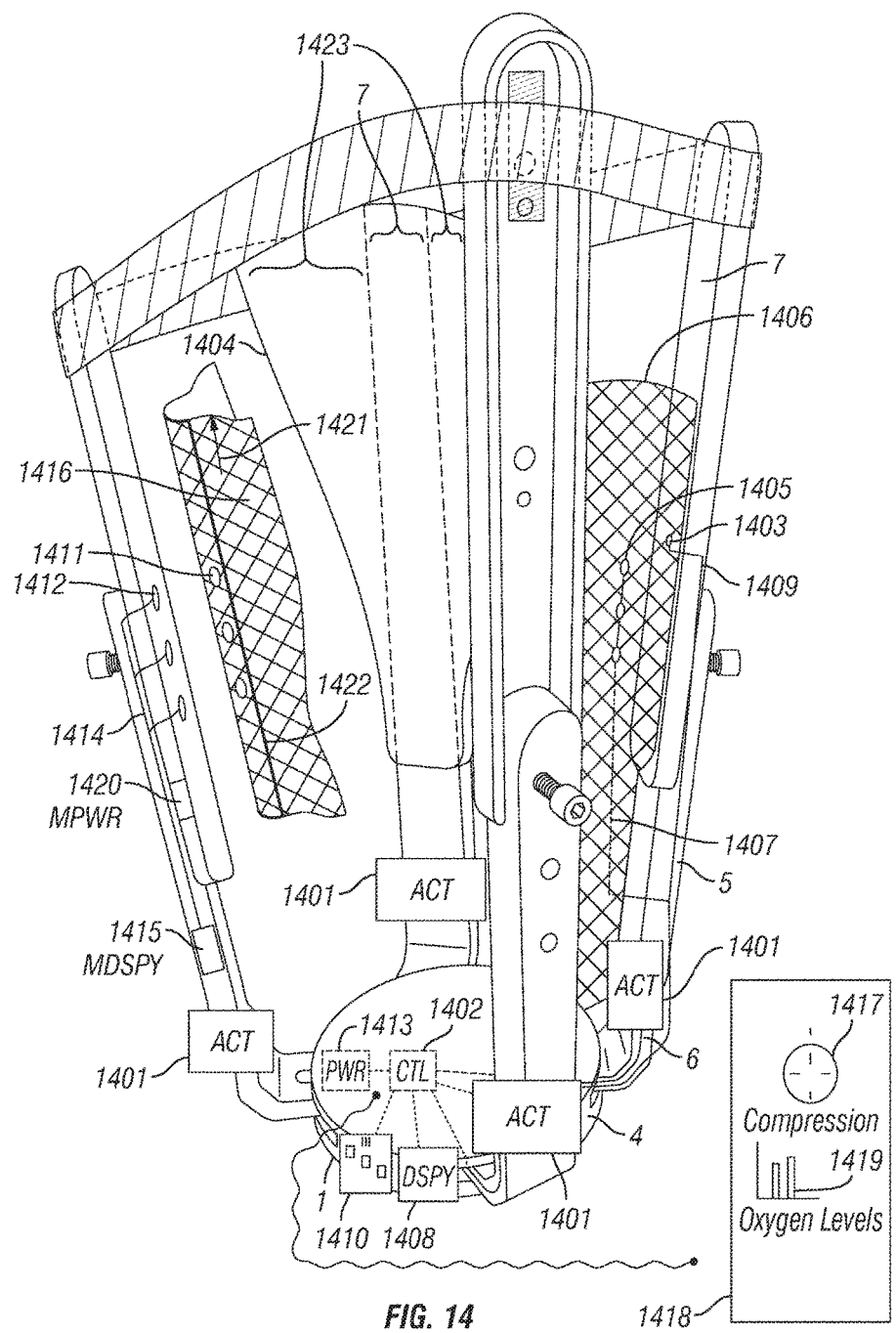
FIG. 14 is a perspective view of a RAS with sensors, a controller, and actuators, and an external smart phone.

In an embodiment depicted in FIG. 14, a rotary actuator 1401 locks the paddles in position upon receipt of a control signal from a controller 1402 indicating that a pressure sensor 1403 has detected that the optimal tissue compression has been obtained.

The embodiment depicted in FIG. 14 also includes an electrical power source 1413 mounted in the adapter 1 to supply power to the controller, actuators, and any other devices requiring power.

It is to be appreciated that other means of locking the components in place may be used, including those where the locking force is applied through pneumatic or hydraulic pressure devices without departing from the spirit and scope of the invention.

It is also to be appreciated that electroactive polymer materials may be configured to substitute for actuators or the paddles themselves to impart optimal tissue compression on the target areas without departing from the spirit and scope of the invention.

Figure 4:
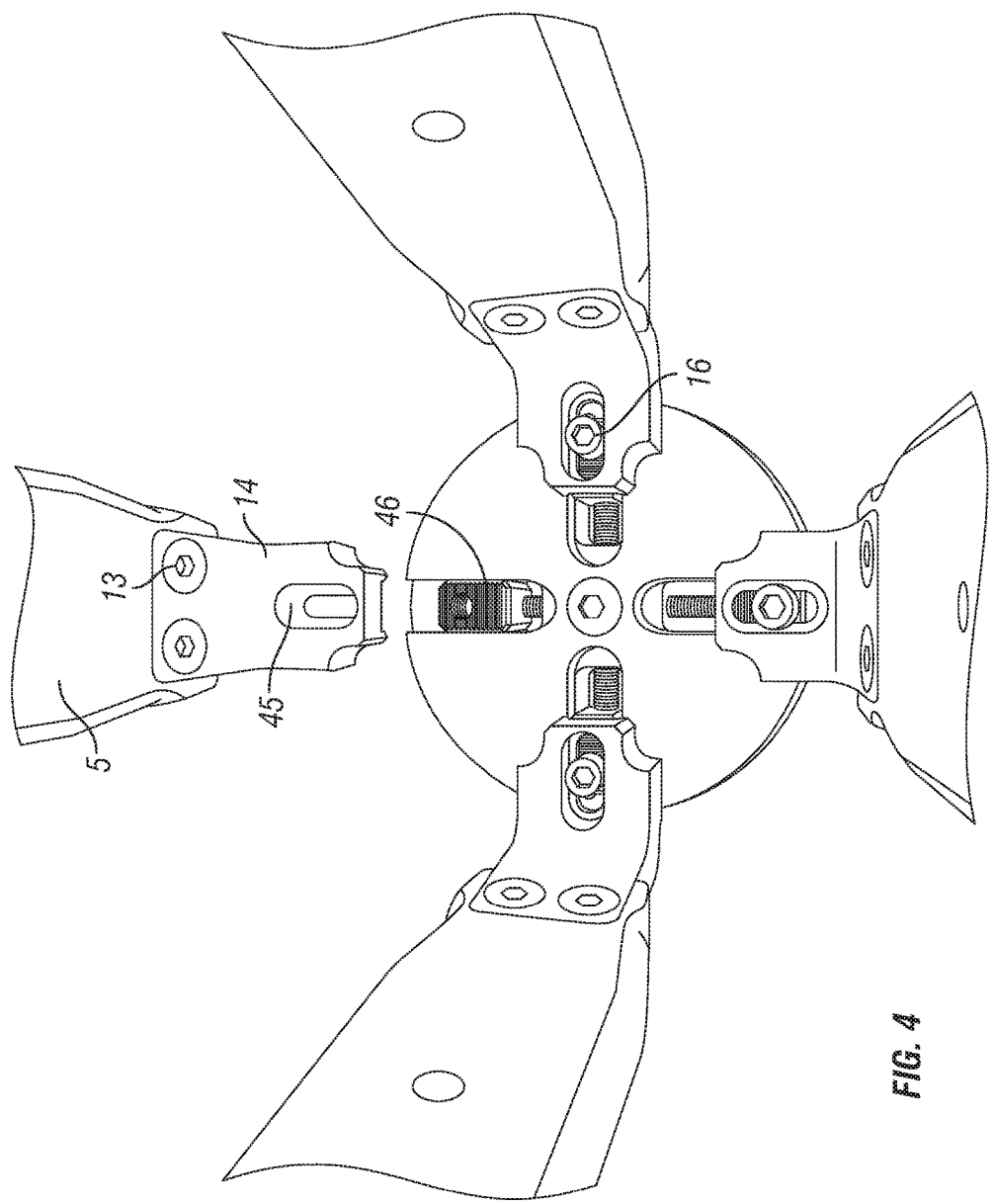
FIG. 4 is a top view of a RAS showing paddle adjustment mechanisms.
Figure 6:
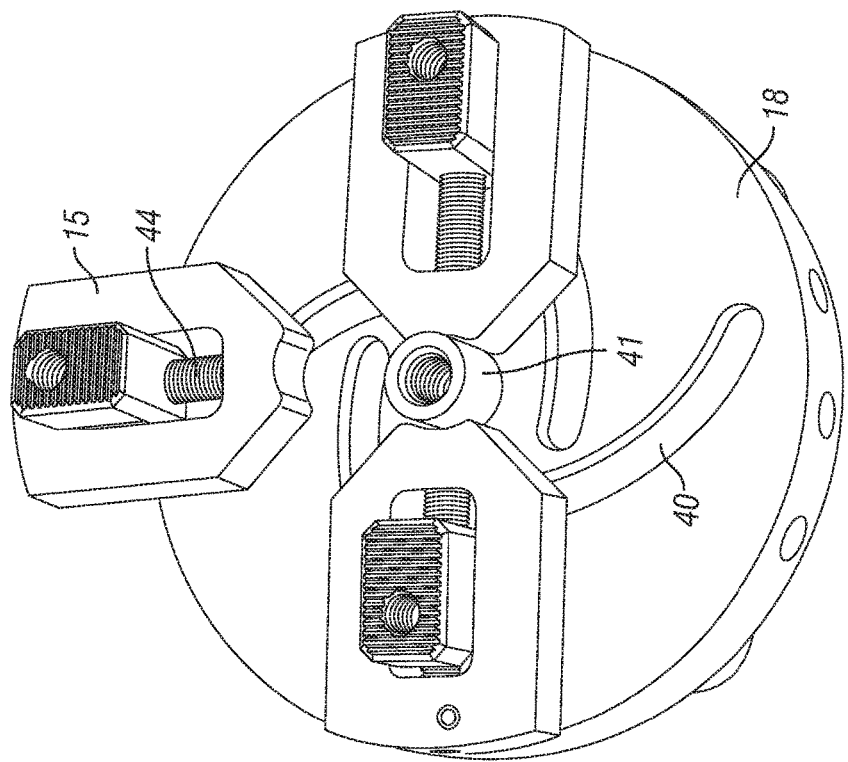
FIG. 6 is a perspective view of a bottom adapter plate.
Figure 7:
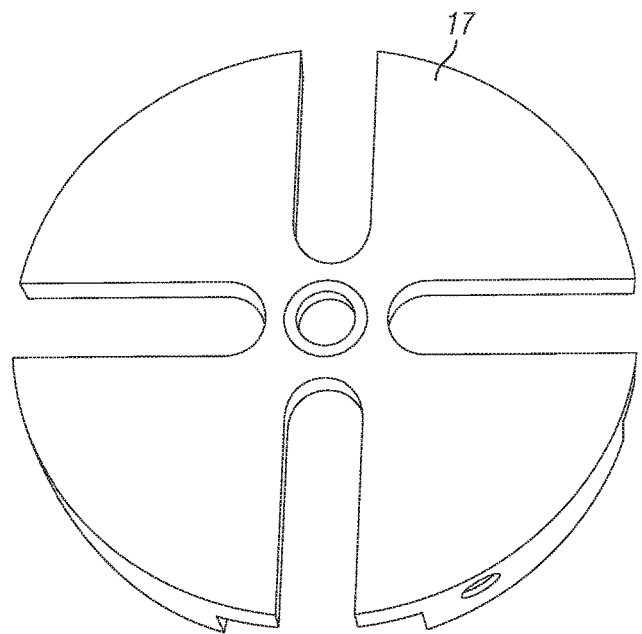
FIG. 7 is a top view of an upper adapter plate.
Figure 8:
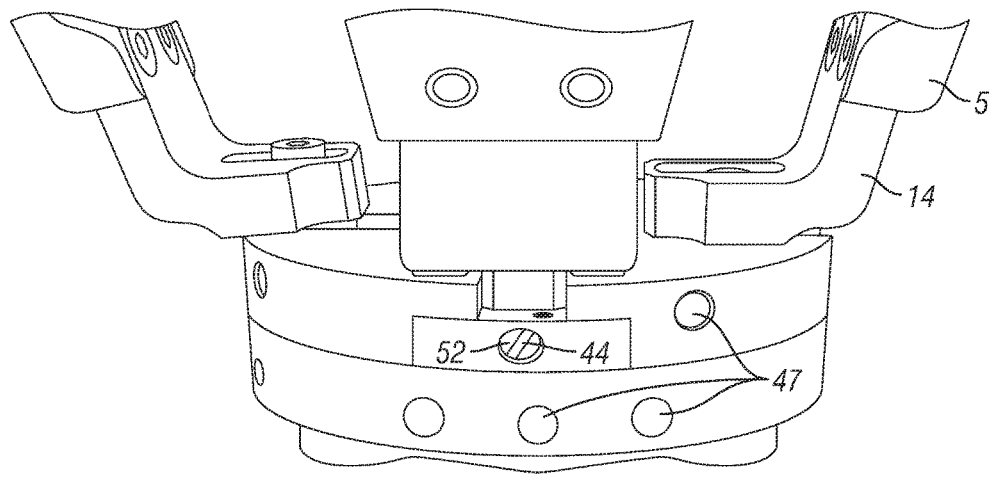
FIG. 8 is a side view of a RAS depicting a fine adjustment leadscrew and outwardly angled preconfigured paddle connectors.

FIGS. 4-11 depict an embodiment where preconfigured paddle connectors are detachable from the paddles. In FIG. 4, the preconfigured paddle connectors 14 can be attached or detached from the paddles 5 using paddle connecting screws 13. Once attached, the preconfigured paddle connectors are sloped inwardly or outwardly from the container center at a variety of fixed angles so that the socket designer may select the preconfigured paddle connectors that best match the shape of the target. For example, FIG. 8 depicts a configuration of the embodiment where the preconfigured paddle connectors 14 are angled outwardly so that the paddles also angle outwardly relative to the center of the container.

FIG. 4 depicts the preconfigured paddle connectors 14 attached to the paddle connector mounts 46, in paddle adjustment mechanisms 15 (shown in FIGS. 6 and 11) using macro adjustment screws 16, shown in FIG. 4. Before fully tightening the macro adjustment screws, the socket designer moves the paddle connectors inwardly or outwardly along the macro adjustment screw slidable coupling track 45, depicted in FIG. 4, to place the paddles in the approximate position necessary to achieve optimal tissue compression. After putting the paddles in this initial compression position, the socket designer tightens the macro adjustment screws to fix the preconfigured paddle connectors in position on the paddle connector mounts.

The paddle adjustment mechanisms 15 in this embodiment use fine adjustment leadscrews 44, depicted in FIGS. 6 and 8, to translate rotational motion applied to the leadscrew heads 52, depicted in FIG. 8, into linear motion. The paddle connector mounts 46, depicted in FIG. 4, serve as leadscrew nuts. Rotation of the leadscrew heads rotate the threaded rod feature of the fine adjustment leadscrews that have been inserted into paddle connector mounts such that when the fine adjustment leadscrews are rotated the paddle connector mounts are moved a selectable linear distance to move the paddle connector mounts inwardly or outwardly from the container center with the effect that the attached paddle moves a corresponding distance and direction. Thus, by rotating the fine adjustment leadscrews, the socket designer or user can make fine adjustments in the paddle position to achieve optimal tissue compression.

Figure 9:
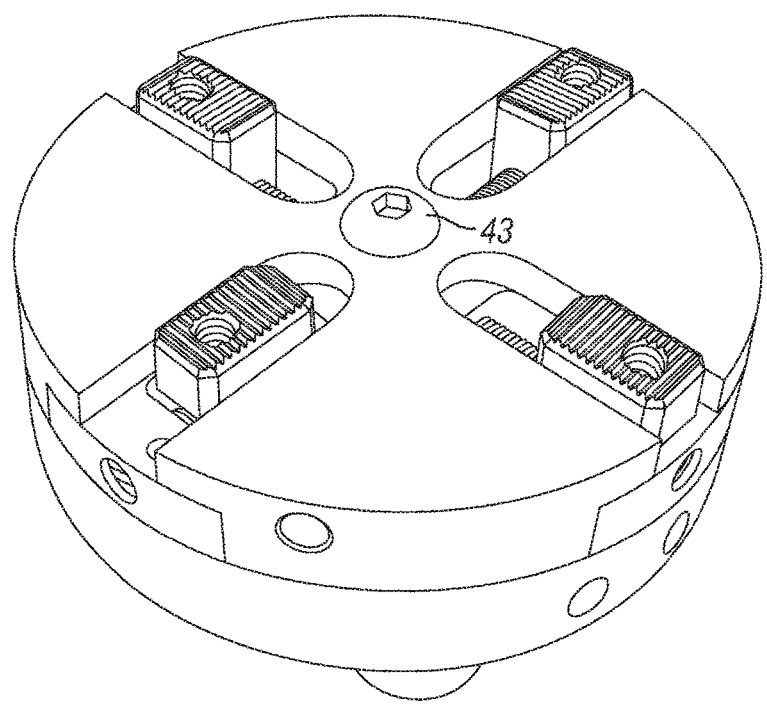
FIG. 9 is a perspective view of an assembled adapter.

FIG. 7 depicts the upper adapter plate 17 separately from the bottom adapter plate 18, depicted in FIG. 6. In FIG. 9, the upper adapter plate is mounted on the bottom adapter plates using a plate connection screw 43. In this and other embodiments, the adapter 1 is also more generally divided between a connector assembly 60 and the prosthetic attachment interface 51, depicted in perspective in FIG. 9 and from the bottom in FIG. 10.

Figure 11:
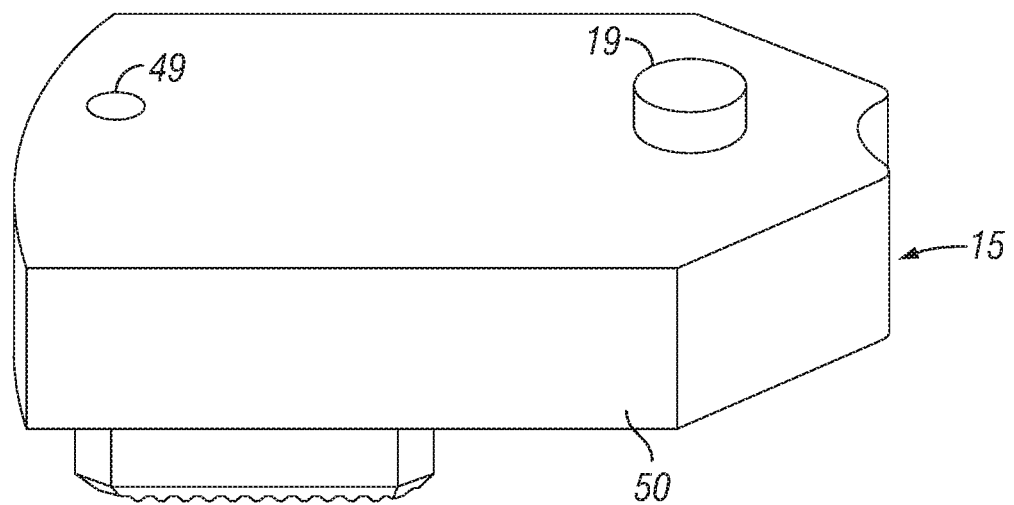
FIG. 11 is a perspective view of a paddle adjustment mechanism.

FIG. 11 depicts a cam follower defined as a paddle adjustment mechanism pin 19 that extends from the bottom of the paddle adjustment mechanism 15. The paddle adjustment mechanism pins follow the cam slides 40 on the top surface of the bottom adapter plate, as depicted in FIG. 6, as the bottom adapter plate is rotated relative to the upper adapter plate around a cam axle 41. This rotation draws the paddle adjustment mechanisms inwardly or outwardly towards or away, respectively, from the center of the container, which, in turn, correspondingly moves the preconfigured paddle connectors 14 and paddles 5, depicted in FIG. 4, inwardly or outwardly from the container center. As depicted in FIG. 8, both the upper adapter plate and bottom adapter plate have cam pin holes 47 in which the socket designer or user can insert cam tightening bars (not shown) for increasing the leverage on the upper and lower adapter plates to rotate each plate with respect to the other plate.

FIG. 11 also depicts a roll pin insertion hole 49 where a roll pin (not shown) is inserted to lock linearly the fine adjustment leadscrew in place by fitting the roll pin into a circumferential groove in the fine adjustment leadscrew once the fine adjustment lead screw is inserted into the paddle adjustment mechanism body 50.

Figure 5:
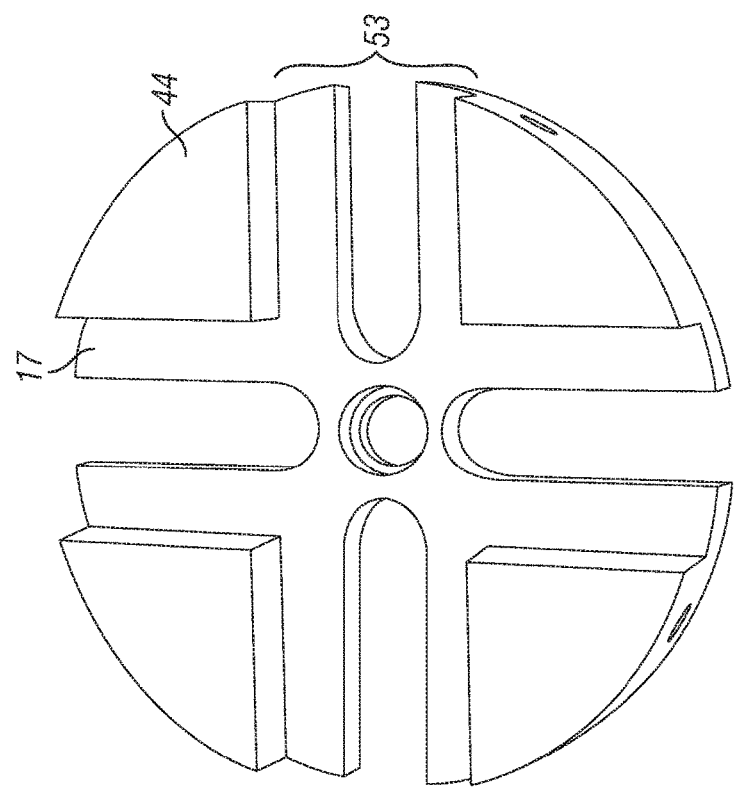
FIG. 5 is a perspective view of the bottom of an upper adapter plate.

FIG. 5 depicts a bottom view of the upper adapter plate 17. When the mating surface 44 of the upper adapter plate is placed on top of the bottom adapter plate 18, shown in FIG. 6, the configuration of the upper adapter plates coupled with the bottom adapter plate creates channels 53 for the movement of the paddle adjustment mechanisms 15 in and out as the paddle adjustment mechanism pins 19 follow the cam slides 40 during rotation of the bottom adapter plate relative to the upper adapter plate.

Figure 10:
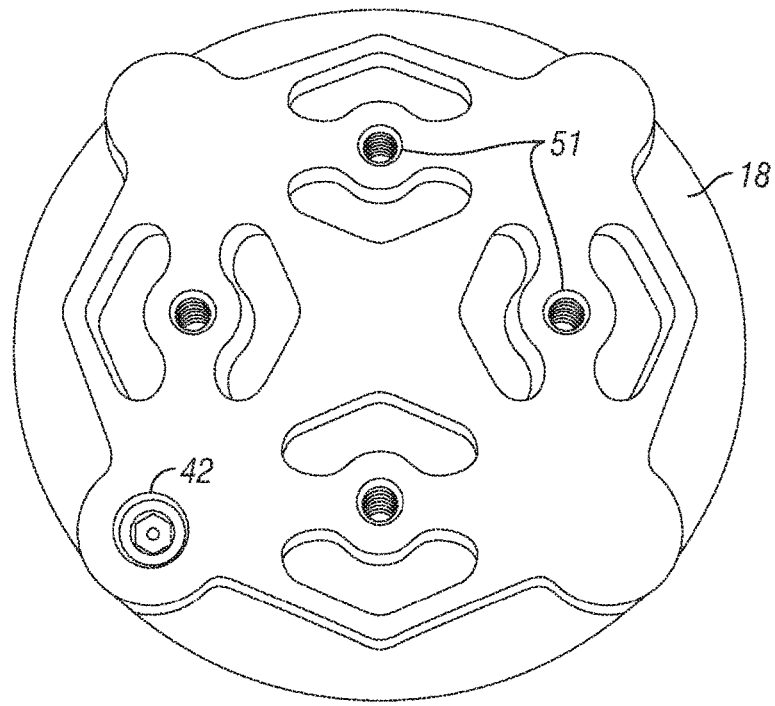
FIG. 10 is a bottom view of a bottom adapter plate.

FIG. 10 depicts the bottom surface of the bottom adapter plate 18, including the cam lock bolt 42. The cam lock bolt locks the bottom adapter plate to the upper adapter plate 17, shown in FIG. 7, to prevent rotation of the plates relative to each other. In the embodiment depicted in FIGS. 4-11, when the plates are rotated relative to each other, the paddle adjustment mechanisms 15 are drawn-in fully or pushed-out fully when the paddle adjustment mechanism pins 19 reach the respective ends of the cam slides 40, simulating the donning or doffing of a traditional socket. When the paddle adjustment mechanism is drawn-in completely, the cam lock bolt in the bottom adapter plate and a correspondingly threaded hole (not shown) in the upper adapter plate line up so that when the cam lock bolt is screwed into the threaded hole, the upper adapter plate is prevented from rotating relative to the bottom adapter plate. This locks the paddles in their fully-in position.

Continuing to identify structures using FIGS. 4-11, in another embodiment of this cam configuration, additional upper adapter plate threaded holes allow partial rotation and locking of the bottom adapter plate 18 relative to the upper adapter plate 17 with the paddle adjustment mechanism pins 19 lying along the cam slides 40, rather than at the ends of the cam slides. The result being that the paddle adjustment mechanisms are drawn partially into or pushed partially out of the channels 53 and locked into place by screwing the cam lock bolt into one of the additional threaded holes. In a variation of this embodiment without the threaded holes, the relative rotation of the upper adapter plate and bottom adapter plate are locked by screwing the cam lock bolt 42 against the bottom of the upper adapter plate to clamp the upper adapter plate to the bottom adapter plate with the pressure from the bolt end. This partial donning or doffing aspect of the invention may be advantageous when a user's activities require less compression, such as while sitting for extended periods of time and the user does not want to lose the fine adjustment screw settings previously established.

FIG. 10 also depicts a four-hole universal prosthetic attachment interface 51 to allow use of the RAS with standard prosthetic devices, such as the prosthetic device 101 depicted in FIG. 1.

In one embodiment (not shown), the socket designer selects from a plurality of paddles of different shapes that are preconfigured to combine the structure and configuration of the paddle and paddle connectors to form a single unit, are directly connectable to the adapter, and preconfigured to slope inwardly or outwardly from the container center at a variety of fixed angles. These preconfigured paddles and the adapter can be part of a kit. The socket designer chooses from the plurality of paddles to best match the shape of the target, for example, one or more of the chosen paddles are angled outward at a particular angle for conical shaped targets. In one embodiment (not shown), the adapter connecting end of the chosen paddles include rails that can slide in and out of the adapter and can be adjustably clamped into a fixed position using adapter clamps to allow the inner surface of the chosen paddles to move towards or away from the container center and, after adjustment, be fixed in the desired position to provide the optimal tissue compression.

Figure 2:
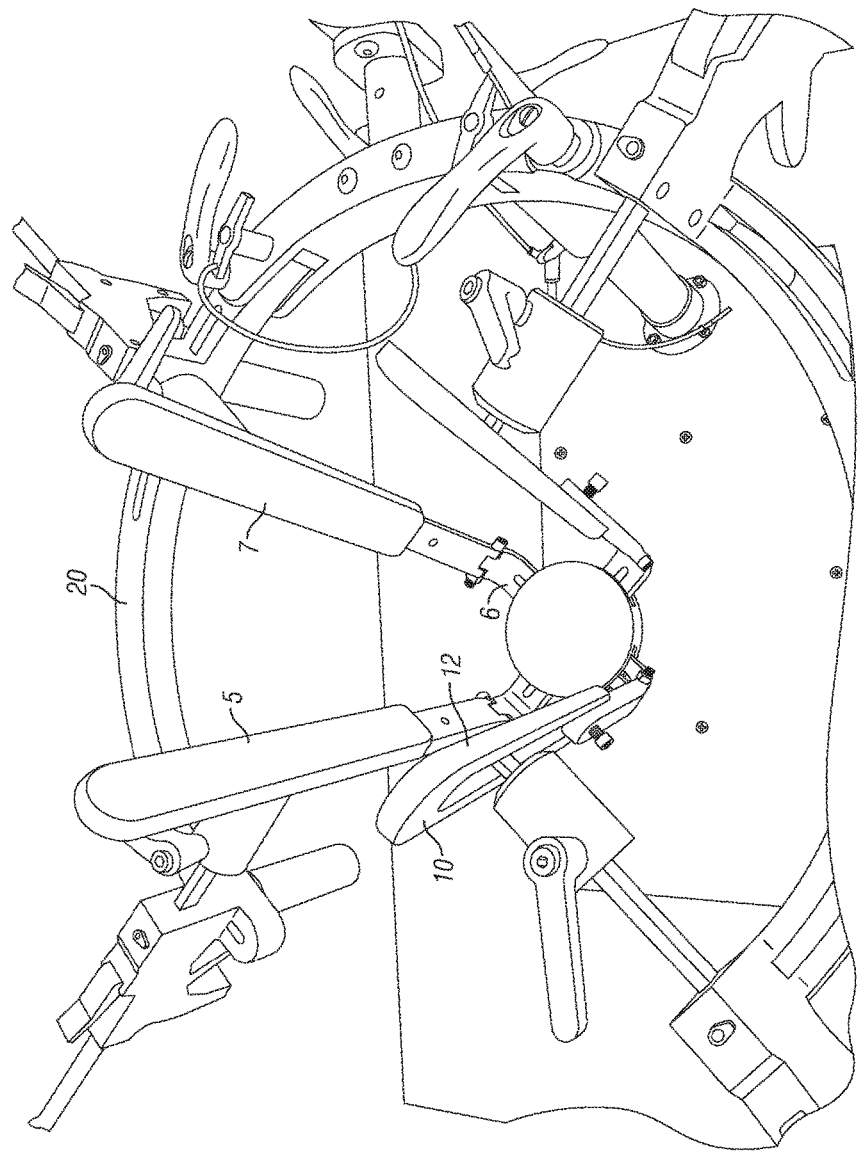
FIG. 2 is a perspective view of a RAS on an external positioning tool.

FIG. 2 depicts an adjustable embodiment of the RAS System including an external positioning tool 20, such as the HiFi™ Imager sold by biodesigns, inc. In this embodiment, the paddles 5 and paddle connectors 6 can be oriented using the external positioning tool to position paddles for optimal tissue compression.

Continuing to identify structures using FIG. 2 reference characters, in some adjustable embodiments, the paddle 5 and paddle connector 6 positions can be adjusted by the user.

In other embodiments, one or more paddle shims can be affixed to the inner surfaces of selected paddles to customize such surfaces to particular characteristics of the target shape. For example, in an embodiment depicted in FIG. 15, a shim 1501 with a thickness tapering across its length is used to customize a paddle inner surface 7 to match the corresponding curvature of the target's underlying skeletal structure. Other shim embodiments in accordance with the principles of the invention include shims of non-uniform widths, lengths, and thicknesses to accommodate unique user body shapes (e.g., conical or bulbous), the presence of bony prominences or neuromas, or to fine tune the fit for an embodiments using paddles selected from a plurality of paddles of different shapes that are preconfigured.

In one embodiment, the shims are made of molded polyurethane, but other suitable materials may be selected without departing from the spirit and scope of the invention.

In a variation to the embodiments described above, stabilizers connect selected paddles 5 to each other at one or more points along their long axes so that they are connected to a portion of the paddles at approximately the paddle end opposite the paddle connectors 6 in order to resist the bending force on the paddles at points distant from the paddle connectors.

FIG. 1 depicts one embodiment of the stabilizer in the form of a ring stabilizer 48 that attaches to the paddles 5 using hook and loop fastener (e.g., Velcro) strips 54, and encircles all the paddles and the relief areas to ring the virtual walls of the container. In this embodiment, the ring stabilizer is attached to the outer paddle surface 10 but the ring stabilizer may be connected to the inner surface 7 or to the paddle sides 12 without departing from the spirit and the scope of the invention.

In the embodiment depicted in FIG. 1, the ring stabilizer 48 is constructed of a hook and loop fastener strap, but flexible, semi-flexible, or rigid materials may be used, including fiberglass, carbon fiber composite, silicone, plastic, aluminum, or electroactive polymer material without departing from the spirit and the scope of the invention.

In another embodiment (not shown), the stabilizers 48 only attach to particular paddles selected by the socket designer and are connected to the outer paddle surface 10 of the associated paddles so that they are connected to a portion of the paddles at approximately the paddle end opposite the paddle connectors 6. In other embodiments, the stabilizers may be connected to the inner surface 7 or to the paddle sides 12 without departing from the spirit and the scope of the invention.

Figure 17:
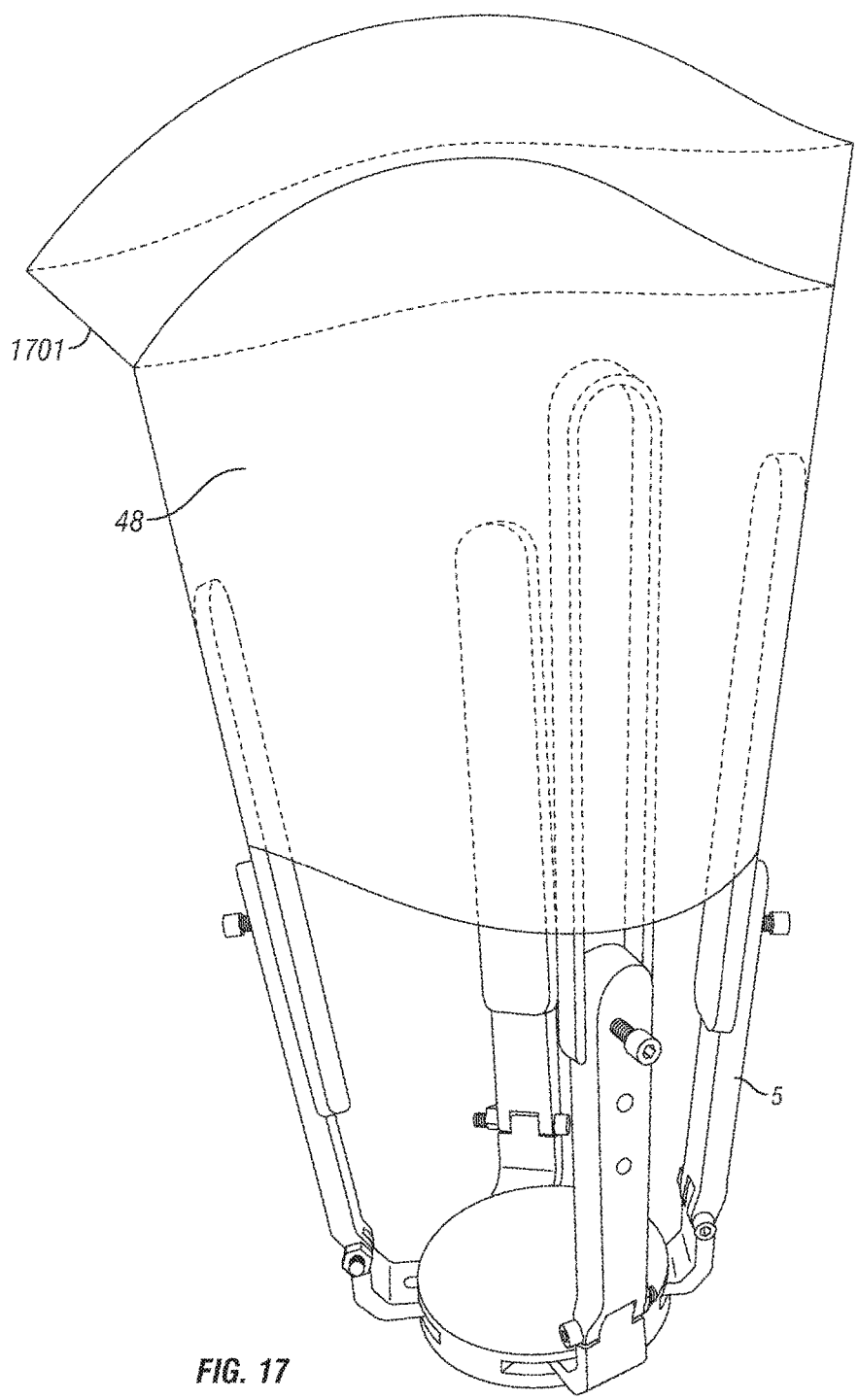
FIG. 17 is a perspective view of a RAS with a large stabilizer.

FIG. 17 depicts an embodiment that uses one or more semi-flexible ring stabilizers and paddles sufficient to resist the bending force on the paddles 5 and connects to a portion of the paddles at approximately the paddle end opposite the paddle connectors 6. In this embodiment, the one or more stabilizers 48 significantly support and contain soft tissue of the target such that under weight-bearing or non-weight-bearing conditions the target is comfortably supported and contained within the RAS in regions selected by the socket designer, for example in the brim area 1701 surrounding the target at the container top, opposite the adapter 1. It is to be appreciated that the one or more stabilizers may overlap each other.

Figure 16:
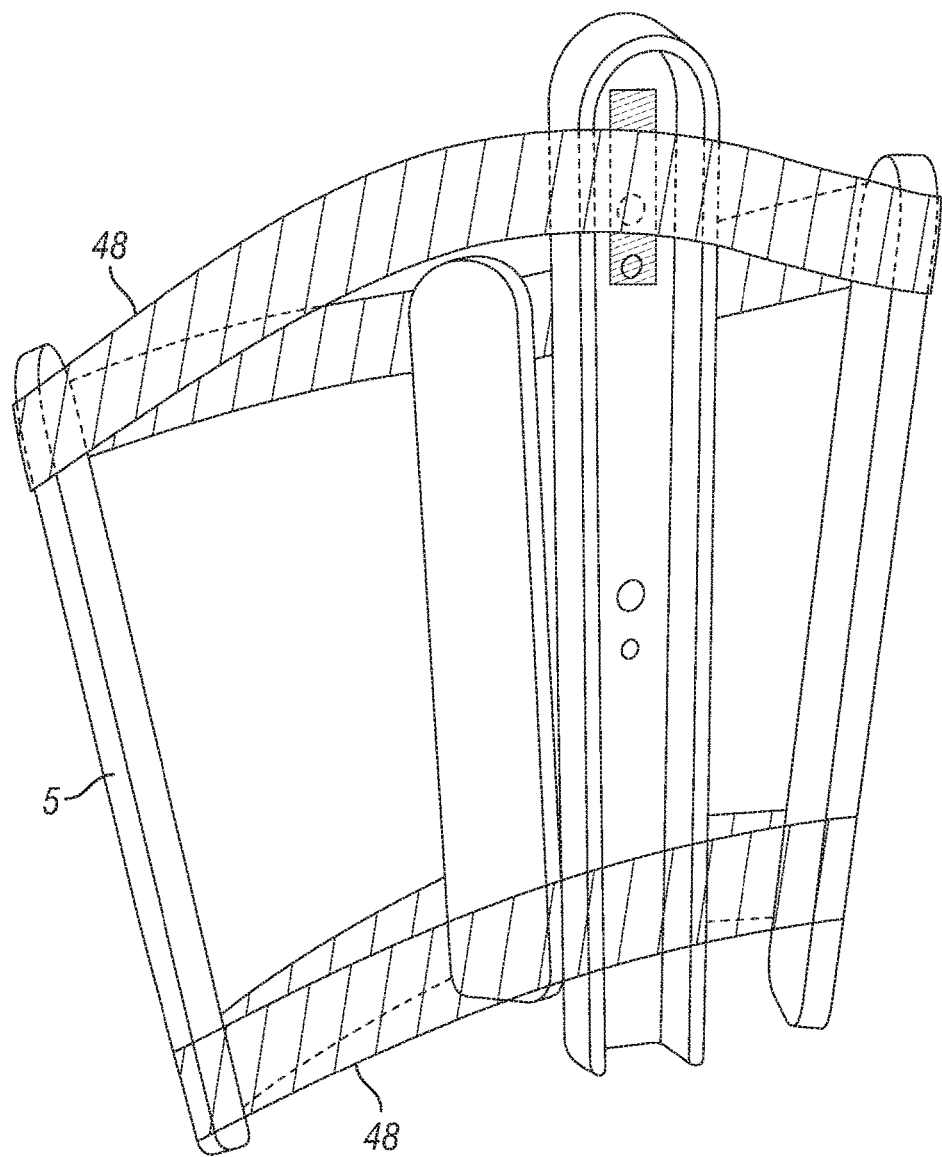
FIG. 16 is a perspective view of a RAS without an adapter.

In one embodiment, depicted in FIG. 16, the adapter is omitted and one or more ring stabilizers 48 cover a portion of each paddle and maintain the relative position of the paddles 5 around the container, which is bottomless with the omission of the adapter. The ring stabilizers shown are constructed of hook and loop fastener straps, but they can be comprised of one or more sections connected with a sliding rail and clamped connectors to allow the user to increase or decrease the compression on the paddles to achieve optimal tissue compression.

Figure 3:
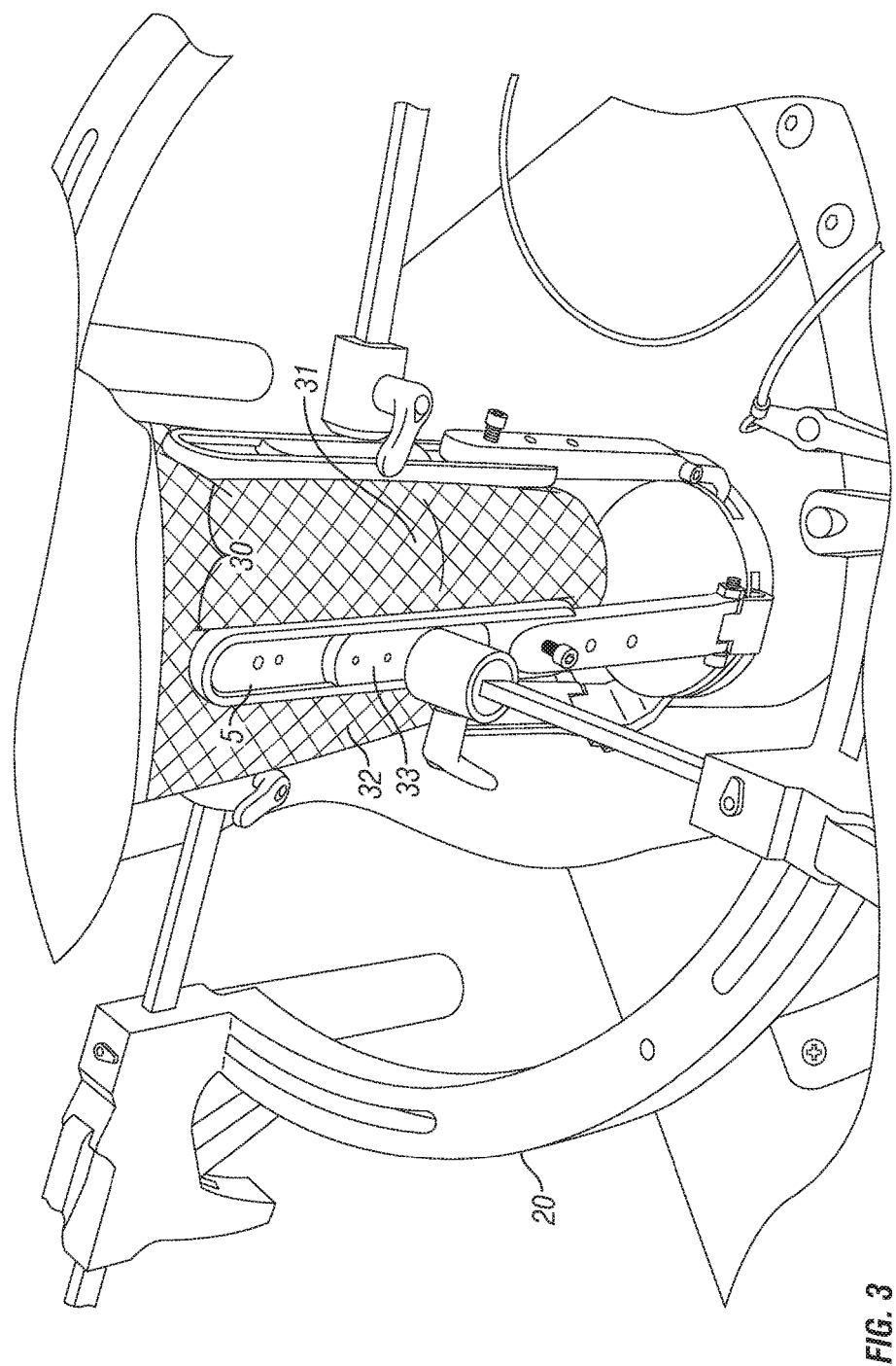
FIG. 3 is a perspective view of a RAS being fitted to an amputee using an external positioning tool.

In one embodiment depicted in FIG. 3, the relief areas allow tissue to flow outward 30 beyond the paddle inner surfaces once compression of the paddles 5 upon the limb is imposed. The volume of tissue that is allowed to flow outward beyond the paddle inner surface is determined by paddle compression levels, the dimensions of the relief areas, the paddle shapes and positions, and whether the target is weight bearing or not and in what fashion (for example, while the user is sitting, standing, walking, running, cycling, hanging, or lifting).

FIG. 14 depicts an embodiment that includes a flared paddle 1404 with an inner surface 7 and support sides 1423 on one or both sides of the inner surface so that the flared paddle is significantly wider at the end furthest from the paddle connectors 6 so that the wider part resists the bending force on the paddle at points distant from the paddle connectors and the support sides support and contain soft tissue of the target such that under weight-bearing conditions the target is comfortably supported and contained within the RAS. It is to be appreciated that the socket designer can select additional paddle shapes and support side width to support other regions of the target to achieve additional bending strength, tissue support, and weight bearing objectives.

Figure 18:
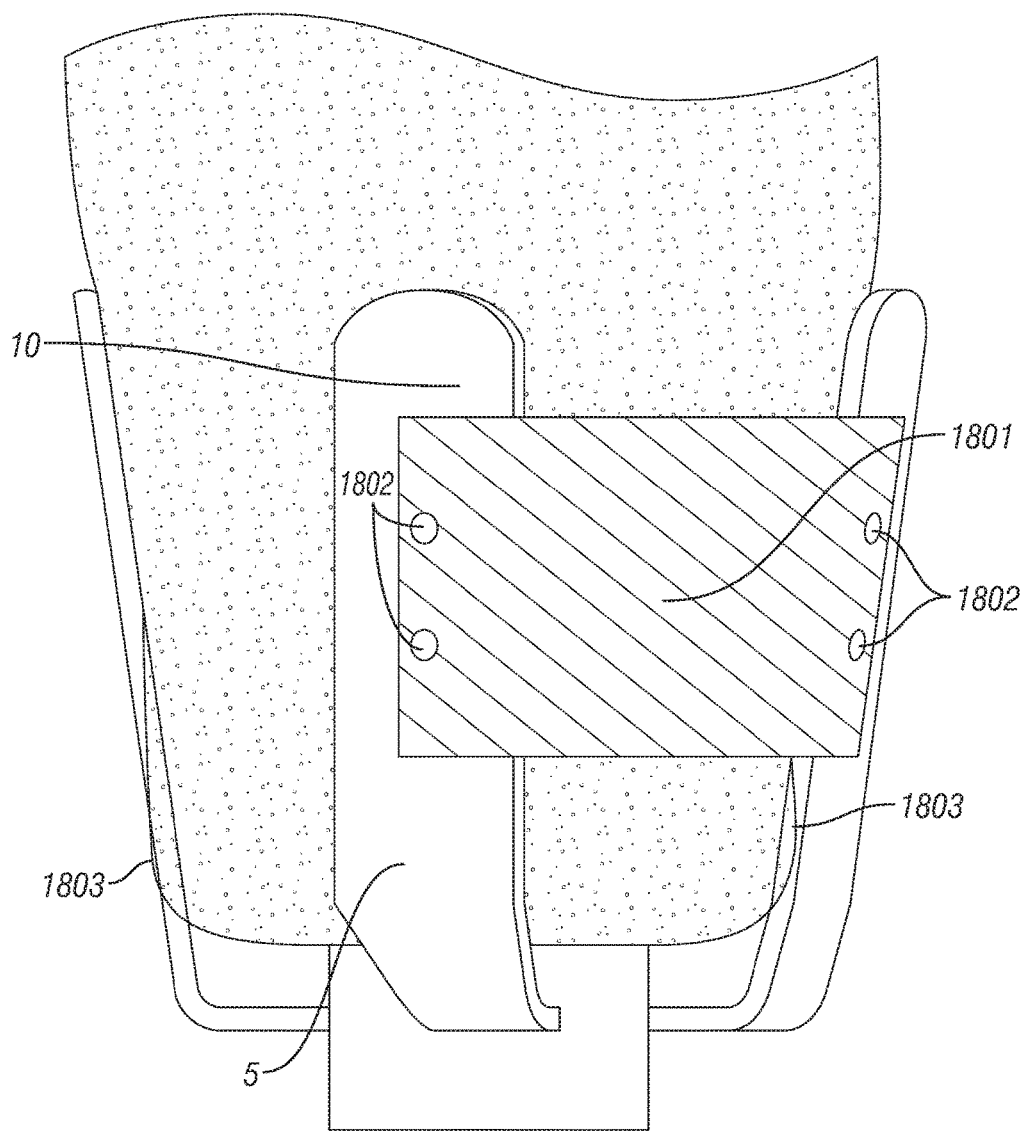
FIG. 18 is a perspective view of a RAS with a single membrane between two paddles.

FIG. 18 depicts an embodiment that includes a membrane 1801 that connects two paddles 5 to each other at a point on the outer surface 10 of each paddle and held by snaps 1802 to limit the outward flow of tissue through the relief areas, but the membrane may be connected to the inner surface 7 or the adjacent paddle sides 11 of each paddle without departing from the spirit and the scope of the invention. In areas not restrained by the membrane in this embodiment, the tissue 1803 is allowed to bulge out.

Figure 19:
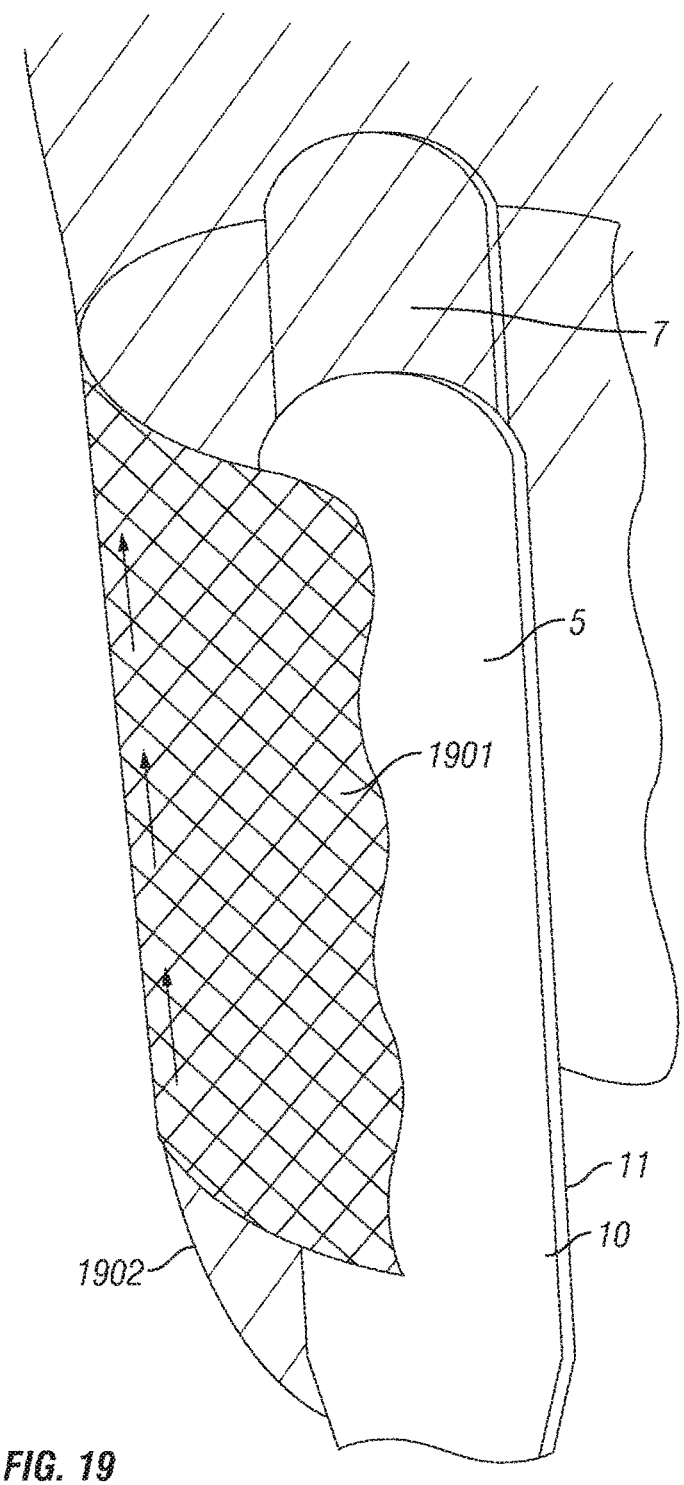
FIG. 19 is a perspective, cut-away view of a RAS with a circumferential membrane.

FIG. 19 depicts an embodiment where the membrane 1901 attaches to the outside surface of the paddles 10 and encircles all the paddles 5 and the relief areas to enclose fully at least a section of the container walls. Alternatively, the membrane may be connected to the paddle inner surface 7 or membrane sections may be predisposed between adjacent paddle sides 11, without departing from the spirit and the scope of the invention.

In one embodiment of the membrane, the membrane lies closer to the adapter 1 than to the stabilizers. However, the membrane may be located at other places along the paddle 5 lengths, without departing from the spirit and scope of the invention.

One embodiment of the membrane is comprised of flexible material such as stretchable fabric. However, embodiments may include semi-flexible or rigid material, without departing from the spirit and the scope of the invention.

The embodiment in FIG. 19 also uses a semi-flexible material for the membrane 1901 that provides upward support and containment of soft tissue 1902 of the target such that, under weight-bearing or non-weight-bearing conditions, the target is comfortably supported and contained within the RAS by controlling, for example, how deep or shallow the target sits or suspends within the RAS.

An additional objective of the membrane is to provide friction upon the released tissue in order to enhance stabilization, control, and suspension by reducing vertical, rotational, and translational motion of the target within the RAS during all phases of the gait cycle and while, for example, the user is standing or sitting.

In one prosthetic embodiment of the RAS depicted in FIG. 3, the paddles 5 are especially configured to interface with a transfemoral limb 31, but the paddles may be configured to interface with other parts of the body, including transtibial, transradial, or transhumeral limbs, without departing from the spirit and the scope of the invention.

Figure 20:
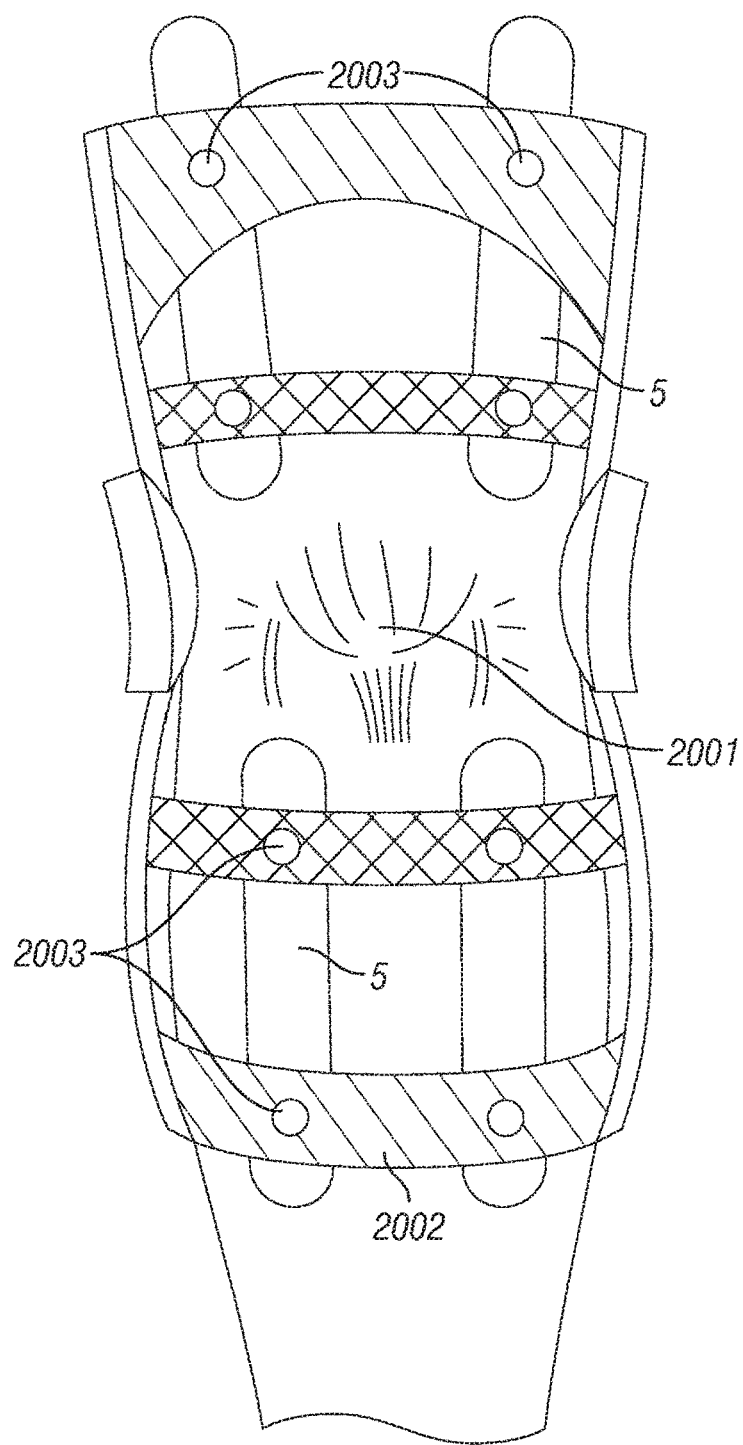
FIG. 20 is a perspective view of a RAS used as a knee brace on an injured joint.

FIG. 20 depicts a knee brace orthotic and orthopedic support device embodiment of the RAS where the paddles 5 are especially configured to interface with an injured knee joint 2001, but in other orthotic or orthopedic support device embodiments, the paddles may be configured to correct or stabilize other body parts without departing from the spirit and the scope of the invention. In the embodiment depicted, the paddles are connected to the knee brace 2002 with thumbscrew compression rods 2003 that screw into and through threaded holes in the knee brace and are rotatably connected to the paddles so that the user can turn the thumbscrews to increase or decrease the compression to achieve optimal tissue compression.

Figure 21:
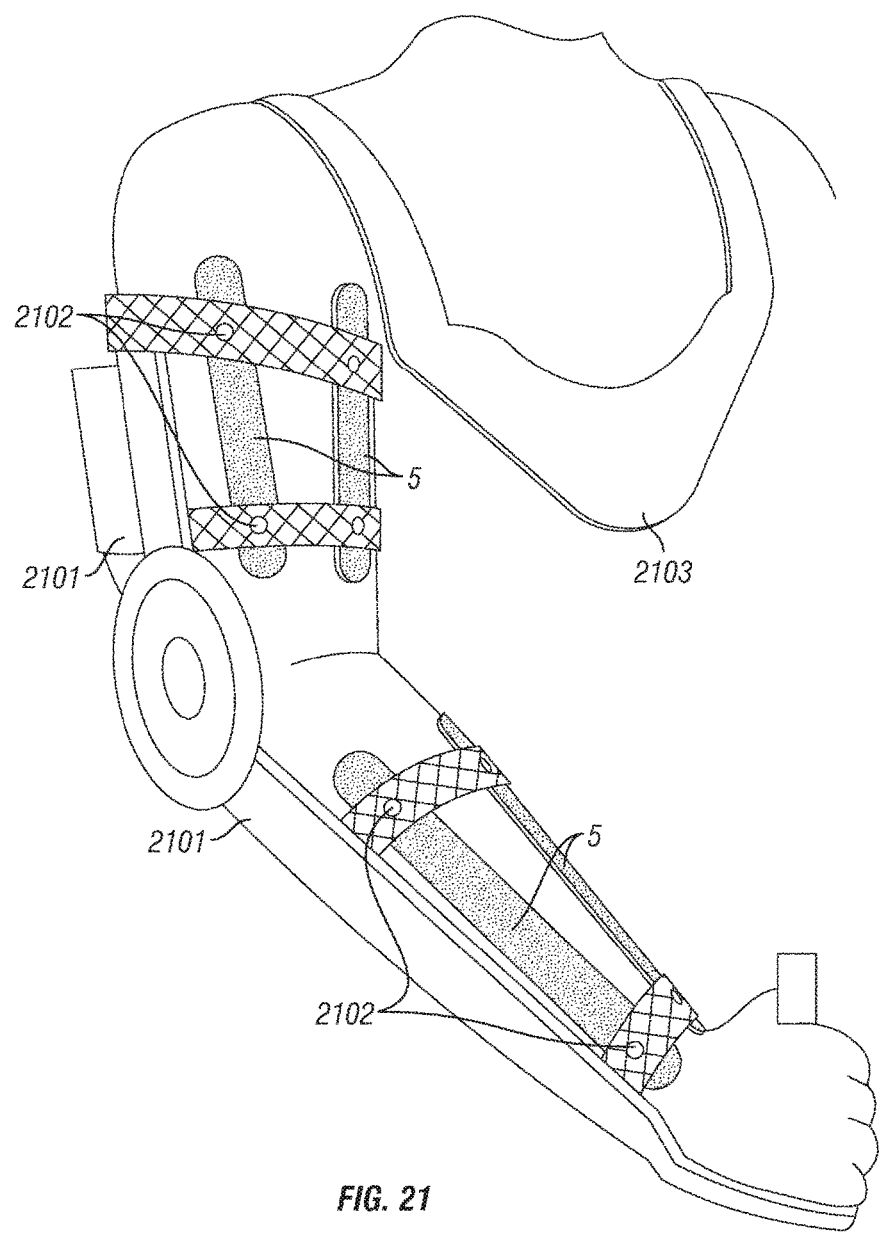
FIG. 21 is a perspective view of a RAS used as an exoskeletal device on an upper limb.

FIG. 21 depicts an upper limb exoskeletal device embodiment of the RAS where the paddles 5 are especially configured to interface with a forearm and upper arm, but in other exoskeletal embodiments, the paddles may be configured to interface with other locations of the body without departing from the spirit and scope of the invention. In the embodiment depicted, the paddles are connected to the upper limb exoskeletal device 2101 with thumbscrew compression rods 2102 that screw into and through threaded holes in the exoskeletal device and are rotatably connected to the paddles so that the user can turn the thumbscrews to increase or decrease the compression to achieve optimal tissue compression. The embodiment depicted also includes a chest support 2103.

In another embodiment, depicted in FIG. 3, the user wears a liner 32 between the target and the RAS so that tissue flow includes flow of the liner, and friction on the skin is replaced with friction on the liner material. In a variation of this embodiment, the liner constrains tissue flow within relief areas by increasing the durometer of the lining material.

The liner may be constructed, for example, out of urethane, silicone, or neoprene based materials.

Some embodiments of the liner fully encapsulate the target as conventionally done and, thus, provide a compressive or elastic force to all of the limb's soft tissue in order, for example, to minimize edema.

Continuing to identify structures using FIG. 3 reference characters, in other embodiments, features of the liner 32 increase the friction or interconnection of the liner and the RAS to enhance stabilization, control, and suspension by reducing vertical, rotational, and translational motion of the target within the RAS and to support and contain soft tissue such that under weight-bearing or non-weight-bearing conditions the target is comfortably supported and contained during all phases of the gait cycle or, for example, while the user is standing, sitting, or lying down.

Figure 22:
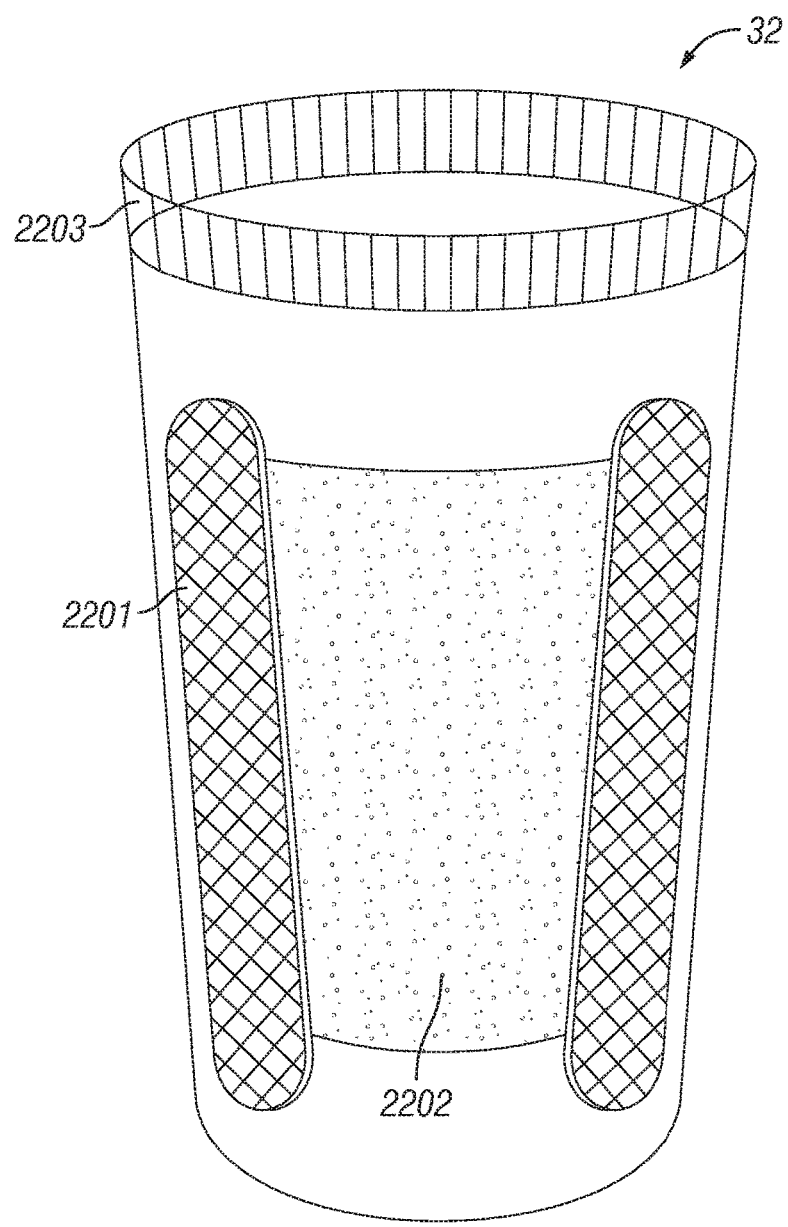
FIG. 22 is a perspective view of a liner with different durometer rings and patches.

FIG. 22 depicts an embodiment where the liner 32 incorporates one or more rings or patches of different durometer to increase or decrease soft tissue support and containment in regions selected by the socket designer, for example, a ring of stiffer durometer material provides tissue support in the brim area 2203 surrounding the target at the container top, opposite the adapter. Similar longitudinal support is provided with longitudinal patches 2201. Substitute material patches 2202 replace and are sewn into sections of the liner where less durometer characteristics are desired.

Figure 15:
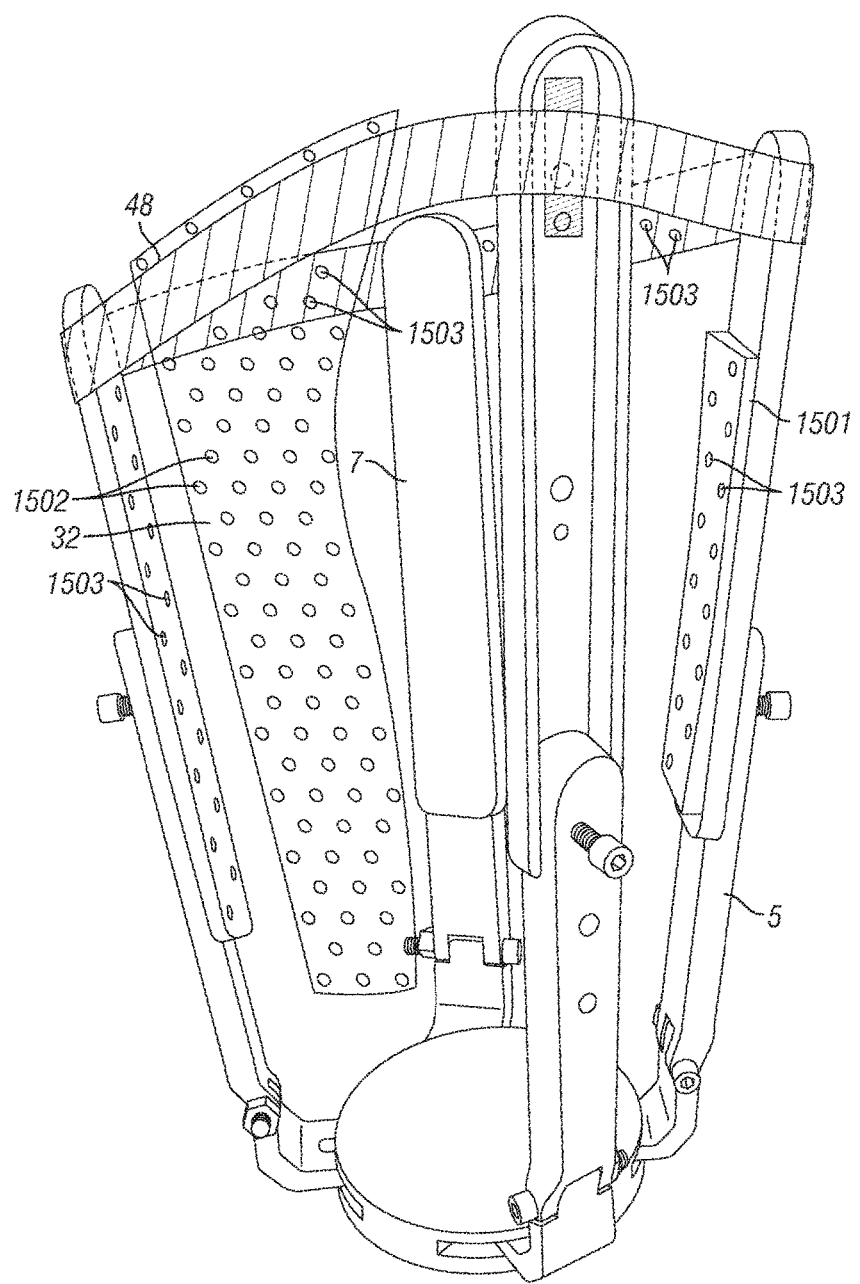
FIG. 15 is a perspective view of a RAS showing a shim, liner, paddles, and stabilizer with raised and recessed features.

In another embodiment, depicted in FIG. 15, the liner 32 has raised bumps 1502 to increase friction with the paddles 5. In a variation of this embodiment, recessed features 1503 on the paddles, stabilizer 48, and membrane (not shown) interlock and increase the friction with the raised features on the liner. The recessed features are also on one or more shims 1501, rather than the paddles to which the shims attach. Alternative embodiments may be configured to have interlocking features such as hook and loop fasteners, interlocking ribs, or magnets of opposing polarity, without departing from the spirit and scope of the invention.

In variations of the embodiments disclosed above, the RAS system includes transducer (e.g., accelerometer, strain gauge, slip detector, pressure sensor, oximeter, angle position sensor, or actuator), processor, amplifier, or memory devices, and a power source for sensing, recording, transmitting, or controlling adapter, membrane, paddle, or stabilizer position, orientation, and relative motion, and physiological parameters of the target (for example, temperature or blood oxygen levels).

For example, FIG. 14 depicts an embodiment where a photometric oximeter 1405 is attached to the inner surface of a membrane 1406, adjacent to the target, where it can detect the oxygen saturation of blood in the target. The oximeter sensor output is sent electronically over a wire communication link 1407 embedded within the membrane and connected through a paddle connector 6 to a controller 1402 mounted in the adapter 1. The controller displays detected oxygen levels on an LCD display 1408 mounted on the adapter side 4.

It is to be appreciated that wireless communication link technologies may be used instead of embedded wires in this embodiment and other embodiments of this disclosure, without departing from the spirit and scope of the invention.

Figure 26:
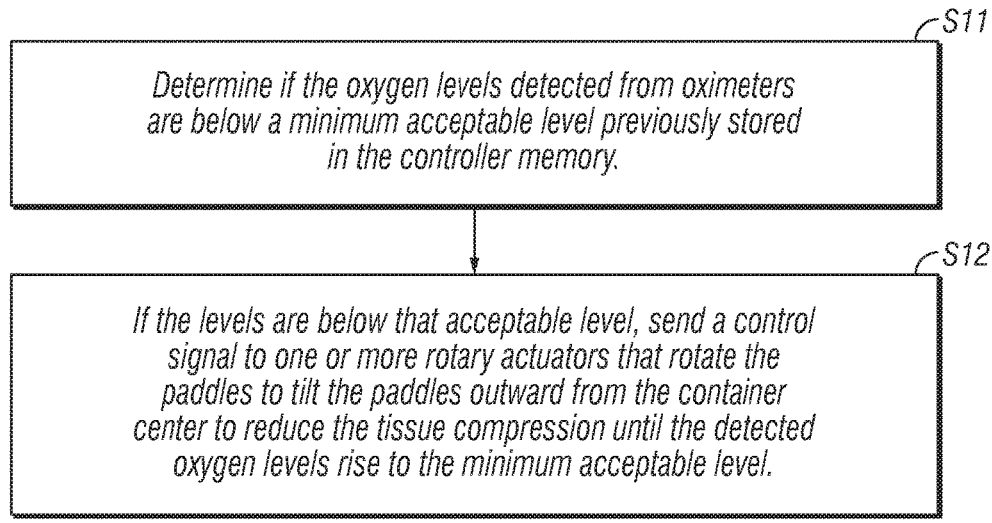
FIG. 26 is a flow chart showing steps in a process of an embodiment of the invention for controlling paddle compression based on oxygen saturation levels.

In a variation of the embodiment depicted in FIG. 14, the controller 1402 mounted in the adapter 1 determines in step S11 of FIG. 26 if the oxygen levels detected from oximeters 1405 are below a minimum acceptable level previously stored in the controller memory. If the levels are below that acceptable level, the controller in step S12 sends a control signal to one or more rotary actuators 1401 that rotate the paddles 5 to tilt the paddles outward from the container center to reduce the tissue compression until the detected oxygen levels rise to the minimum acceptable level.

The embodiment depicted in FIG. 14 also has one or more pressure sensors 1403 that are attached to the inner surface 7 of one or more paddles 5, adjacent to the target, where the pressure sensors can sense the pressure between the paddles and the target. The pressure sensor outputs are sent electronically to the controller 1402 mounted in the adapter 1 via a wire communication link 1409 running along and attached to each paddle and paddle connector 6. The controller converts the pressure sensor output to the controller to a control signal from the controller in order to display detected pressure levels on one or more LCD displays 1408 mounted on the adapter side 4.

In a variation of this embodiment, the user or socket designer manually positions the paddles 5 over selected skeletal structures prior to applying tissue compression and observes pressure readings as pressure is applied in order to determine the relative compression of the paddles over the underlying skeletal structure to determine optimum fit.

Figure 27:
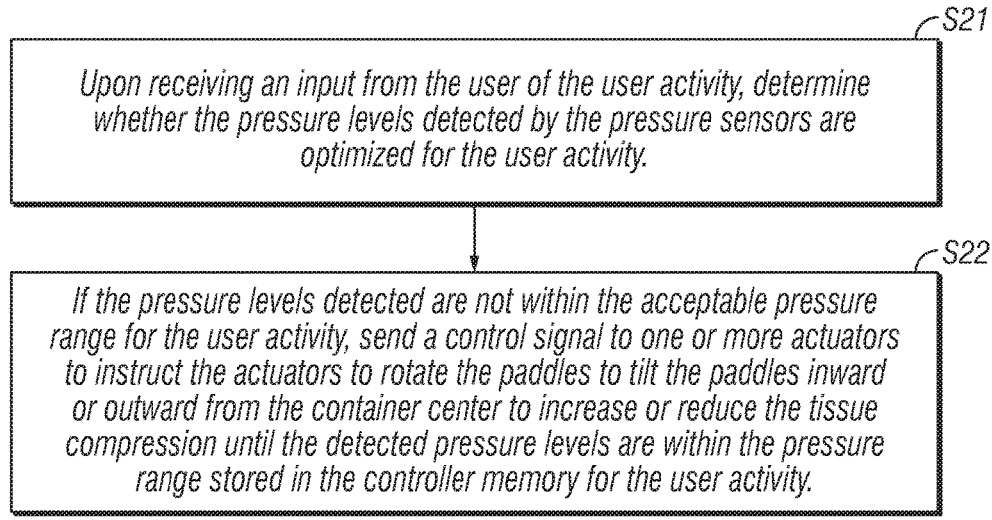
FIG. 27 is a flow chart showing steps in a process of an embodiment of the invention for controlling paddle compression based on pressure levels.

FIG. 14 also depicts an embodiment where the controller 1402 determines in step S21 of FIG. 27 whether the pressure levels detected by the pressure sensors 1403 are optimized for the user activity that the user selects through a set of user operable control input buttons on an input device 1410 mounted on the side of the adapter 1. User activities include, for example, resting, walking, running, or lifting. Each control button corresponds to an optimum pressure range stored for that user activity in the controller memory. In step S22, if the pressure levels detected are not within the acceptable pressure range for the user activity, the controller sends a control signal to one or more actuators to instruct the actuators to rotate the paddles 5 to tilt the paddles inward or outward from the container center to increase or reduce the tissue compression until the detected pressure levels are within the pressure range stored in the controller memory for the user activity.

Figure 28:
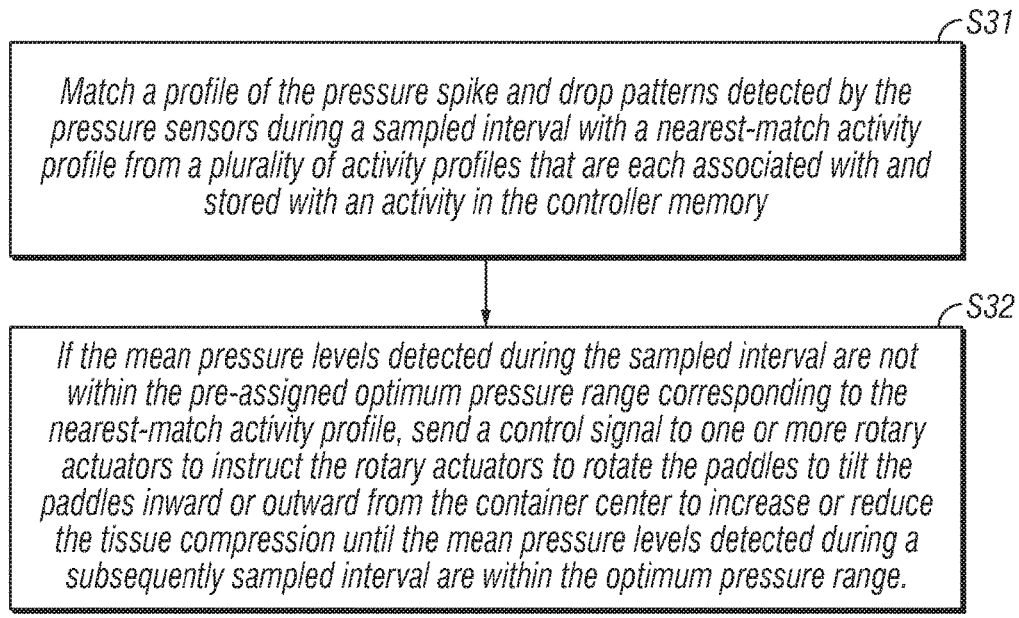
FIG. 28 is a flow chart showing steps in a process of an embodiment of the invention for controlling paddle compression based on detected pressure patterns and levels.

In a variation of the embodiment depicted in FIG. 14, the controller 1402 matches, in step S31 of FIG. 28, a profile of the pressure spike and drop patterns detected by the pressure sensors 1403 during a sampled interval with a nearest-match activity profile from a plurality of activity profiles that are each associated with and stored with an activity in the controller memory, where each activity in the controller memory is pre-assigned an optimum pressure range for that particular activity. If the mean pressure levels detected during the sampled interval are not within the pre-assigned optimum pressure range corresponding to the nearest-match activity profile, the controller, in step S32, sends a control signal to one or more rotary actuators 1401 to instruct the rotary actuators to rotate the paddles 5 to tilt the paddles inward or outward from the container center to increase or reduce the tissue compression until the mean pressure levels detected during a subsequently sampled interval are within the optimum pressure range.

In one embodiment of this variation, the sample interval is 100 milliseconds and the sampling is repeated every 500 milliseconds.

Figure 29:
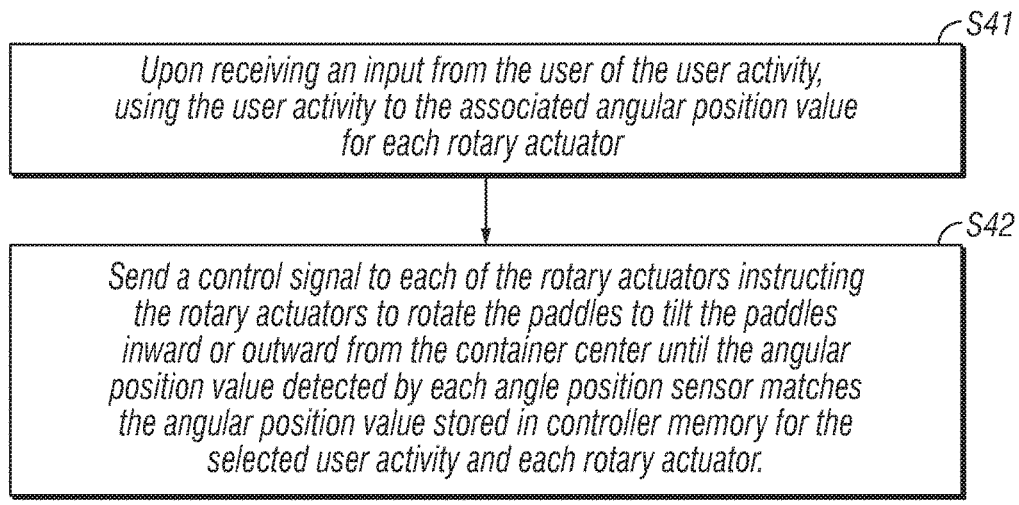
FIG. 29 is a flow chart showing steps in a process of an embodiment of the invention for controlling paddle compression based on paddle angles relative to associated paddle connectors.

In a variation of the embodiment with the manually selectable activities depicted in FIG. 14, each user activity is associated with an angular position value stored in controller memory for each rotary actuator 1401, wherein the angular position is the angle between each paddle 5 and each paddle connector 6 that achieves optimal tissue compression for the user activity. Upon receiving an input from the user of the user activity using the user operable control input buttons on the input device 1410, the controller, in step S41 of FIG. 29, matches the user activity to the associated angular position value for each rotary actuator and, in step S42, sends a control signal to each of the rotary actuators 1401 instructing the rotary actuators to rotate the paddles to tilt the paddles inward or outward from the container center to increase or reduce the tissue compression until the angular position value detected by each angle position sensor (not shown) coupled to each rotary actuator matches the angular position value stored in controller memory for the selected user activity and each rotary actuator.

Figure 23:
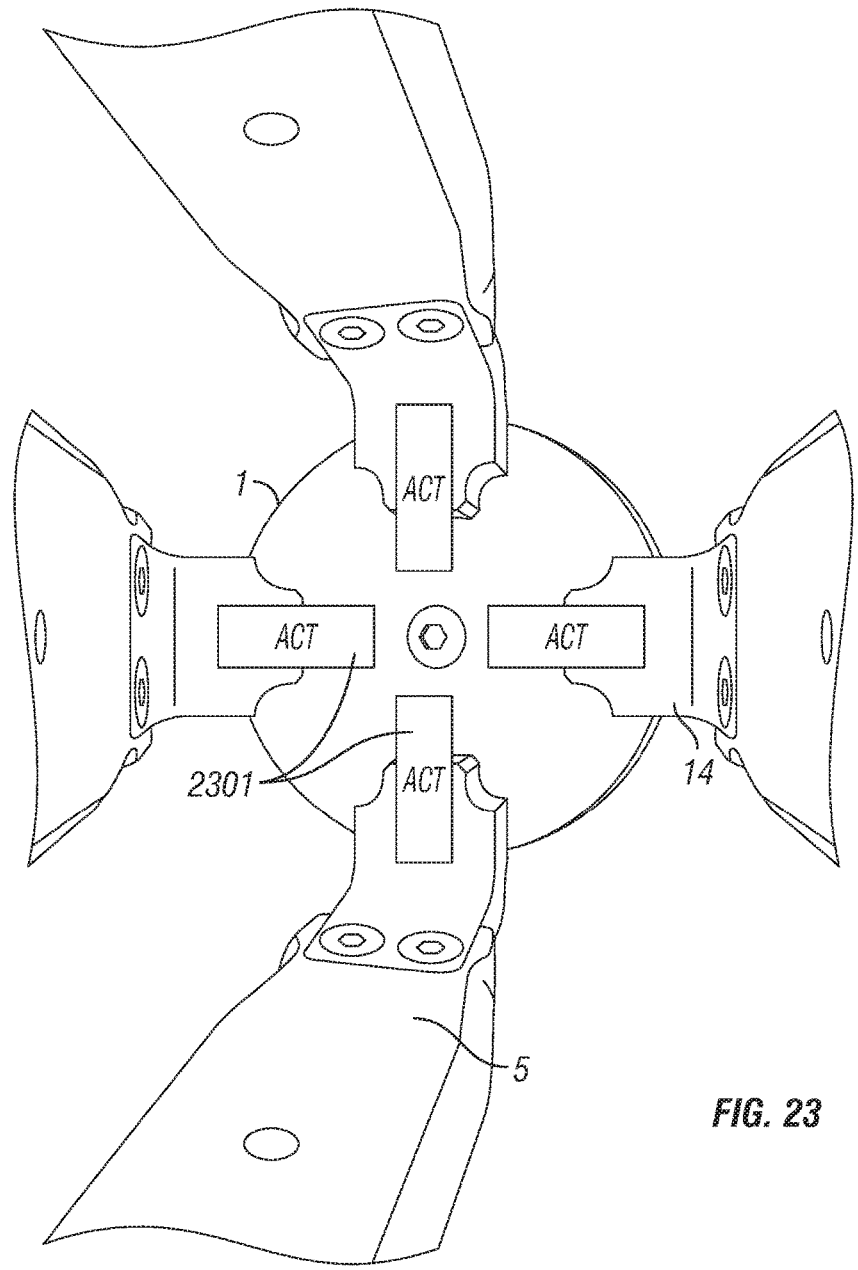
FIG. 23 is a perspective view of a RAS with linear actuators.

FIG. 23 depicts a preconfigured paddle connector embodiment configured with linear actuators 2301 attached to the adapter 1 and connectable to the preconfigured paddle connectors 14 to slide the paddles 5 in or out of the adapter sides to adjust paddle compression.

In one embodiment, depicted in FIG. 14, the liner 1416 may include one or more liner magnets 1411 that the user can align with bony prominences or other readily locatable physical features of the target such that magnetic field sensors 1412 mounted along with a magnetic field sensor power source 1420 on a paddle 5 can be consistently positioned by the user over the target area. When the paddle is properly aligned with the liner magnets, all the magnetic fields meet the magnetic field sensor detection thresholds. As a result, the magnetic field sensors send display signals over a wire communication link 1414 to an LED display 1415 mounted on the paddle and configured to indicate to the user that the paddle is in the proper position relative to the target area.

In a variation of this embodiment, depicted in FIG. 14, the liner 1416 is visibly marked with a physical feature alignment marking 1421 that the user can align with bony prominences or other readily locatable physical features of the target (not shown). Once so aligned, this embodiment is configured so that a target area marking 1422 will provide an outline to the user where to place a paddle so that the paddle is in the proper position relative to the target area.

The several embodiments disclosed herein illustrate some of a variety of embodiments within the spirit and scope of the invention that utilize sensors, actuators, computer memory, and microprocessor devices to monitor and control the components of the RAS. Besides the orientation of the paddles described above, such electronics may also be readily adapted to monitor and control the membrane and stabilizers using the principles of the invention.

Figure 24:
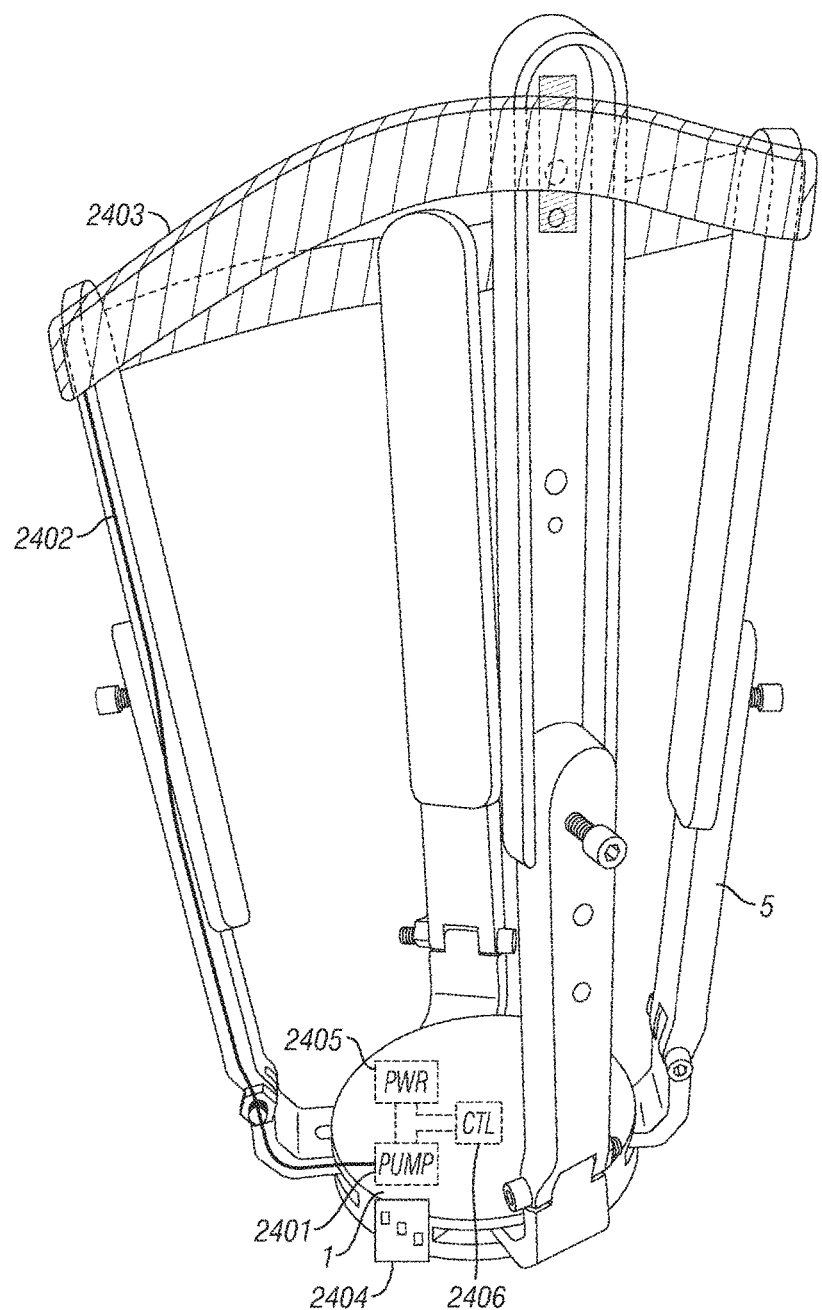
FIG. 24 is a perspective view of a RAS with an inflatable ring stabilizer cuff, input device, and a controller.
Figure 30:
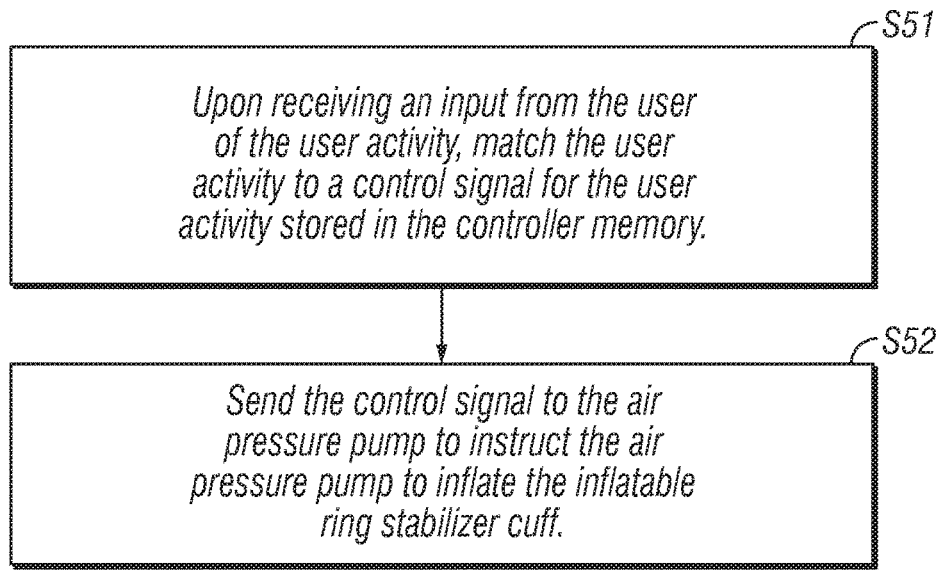
FIG. 30 is a flow chart showing steps in a process of an embodiment of the invention for controlling an inflatable ring stabilizer cuff.

FIG. 24 depicts an embodiment that includes an air pressure pump 2401, air tube 2402, inflatable ring stabilizer cuff 2403, power source 2405, and controller 2406. In this embodiment, the user selects user activities through a set of user operable control input buttons on an input device 2404 mounted on the side of the adapter 1. In step S51 of FIG. 30, the controller matches the user input to a control signal for the user input stored in the controller memory. User activities include, for example, resting, walking, running, or lifting. In step S52, the controller sends the control signal to the air pressure pump to instruct the air pressure pump to inflate in accordance with the control signal, via the air tube, the inflatable ring stabilizer cuff encircling the paddles 5.

The control signal and resultant air pressure is predetermined for each user activity to minimize the loss of paddle compression over the length of the paddles due to the bending force on the paddles from the force or movement of the target for the user activity.

Figure 25:
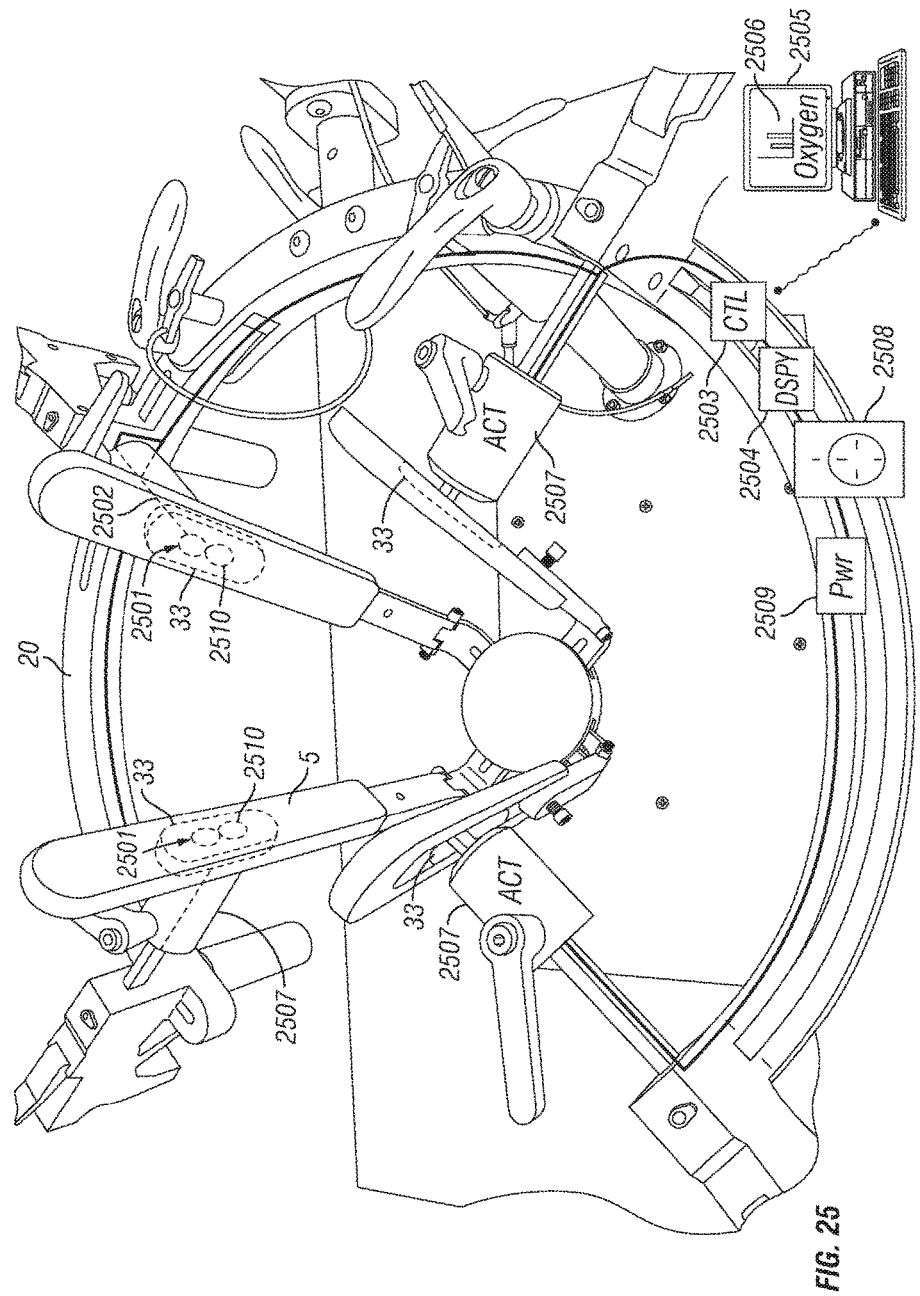
FIG. 25 is a perspective view of a RAS and RAS fitting tool with sensors, controller, and actuators, and an external general purpose computer.

FIG. 25 depicts an external positioning tool device embodiment that includes sensors, so that the RAS itself does not require sensors or other electronics. Rather, the RAS is adjusted and its components locked in place by a socket designer using sensors mounted on the position tool device. In this embodiment, the position tool 20 includes compression bars 33 (as similarly depicted in FIG. 3) that attach to the outside of the paddles 5. One or more pressure sensors 2501 are attached to the compression bars of the position tool so that the pressure sensors are situated between each compression bar and paddle in order to measure the pressure between the compression bars and the paddles. When the paddles are compressed against the target by applying pressure on the paddles by pressing the compression bars against the paddles, the pressure sensors output electronically over a wire communication link 2502 attached to each compression bar and further connected through the external tool to a controller 2503 mounted on the external tool. The controller sends a control signal to a LCD display 2504 mounted on the external tool to display detected pressure levels. The embodiment includes oximeter sensors 2510, in addition to the pressure sensors, but the embodiment may use oximeter sensors exclusively, or a different sensor useful for optimizing performance, without departing from the spirit and scope of the invention.

In a variation of this embodiment, the controller 2503 is configured to communicate wirelessly over a communication link with a general purpose computer 2505 especially programmed to receive the controller input and to display the pressure or oxygen levels on a computer screen 2506.

It is to be appreciated that a desktop or laptop computer may also be used to program the controller mounted on either an external tool or the RAS via a wired or wireless communication link. A smart phone or tablet computer may also be used to perform the same function as the desktop or laptop computer.

In the embodiment depicted in FIG. 25, the external tool's compression bars 33 are controlled by linear actuators 2507 that apply a force specified by the operator through an operator input device 2508. The operator input device depicted is an optimal tissue compression selecting dial mounted on the external tool 20 and operable to take the voltage input from a power source 2509 and vary the voltage output to the linear actuators to press with variable pressure on the compression bars against the paddles 5 to the optimal tissue compression selected. A variation of this embodiment includes incorporating the pressure sensors between the compression bars and the paddles. The pressure sensors send detected pressure levels to controller 2503. The controller sends a control signal to a LCD display 2504 to display actual measured pressure levels.

In a further variation of this embodiment, a computer 2505 controls an adjustable voltage regulator circuit so that the computer and the adjustable voltage circuit substitute for the optimal tissue compression selecting dial 2508 for purposes of controlling the linear actuators 2507.

Figure 31:
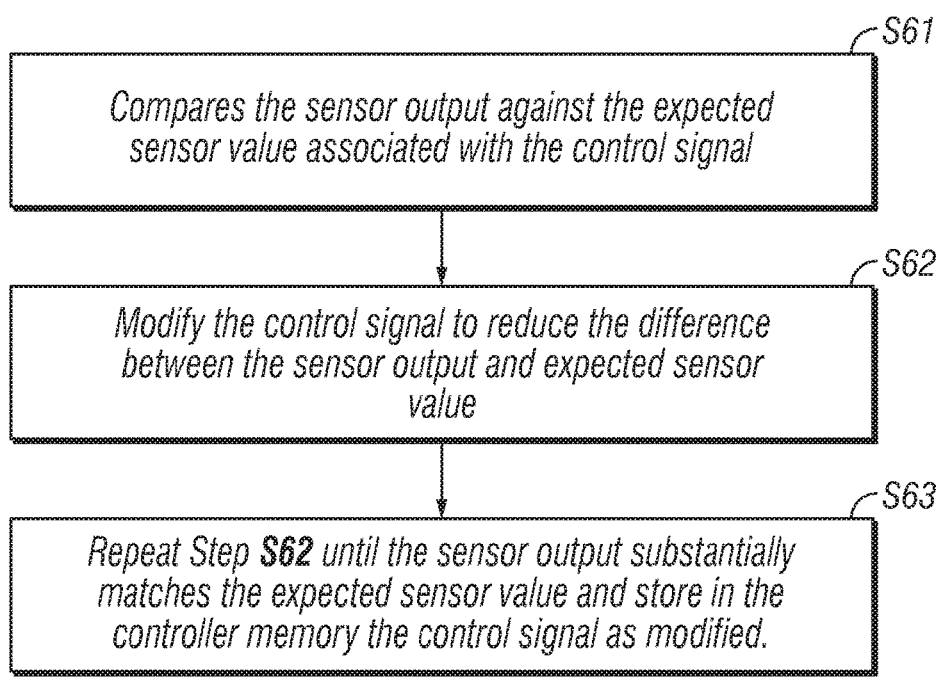
FIG. 31 is a flow chart showing steps in a process of an embodiment of the invention for self-calibrating control signals based on actual pressure level readings.

Another embodiment with a pressure sensor 2501 between a compression bar 33 and a paddle 5 provides a feedback loop to the controller 2503 for self-calibration of the control signal, as depicted in FIG. 25 and FIG. 31. In step S61, the feedback loop compares the sensor output to the controller after the controller sends a control signal to an actuator 2507 against the expected sensor value associated with the control signal, where the expected sensor value and the control signal are associated and stored in the controller memory. In step S62, the controller modifies the control signal to reduce the difference between the sensor output and expected sensor value until, in step S63, the controller determines the sensor output substantially matches the expected sensor value and the controller stores in the controller memory the control signal as modified.

It is to be appreciated that a controller, adjustable voltage regulator, actuators, power source, and pressure sensors may be configured and mounted on the RAS itself to achieve self-calibrating, optimal tissue compression.

FIG. 14 depicts a variation of the optimal tissue compression selecting dial embodiment in which a two dimensional representation 1417 of that dial is displayed on a touch screen on a smart phone 1418. The smart phone is programmed to allow a RAS user to instruct over a wireless communication link a controller 1402 mounted on the RAS, to increase or decrease the voltage to the rotary actuators 1401. The rotary actuators are configured to compress or release the paddles 5 so that the user can self-regulate the compression according to the user's need to control lost motion in the RAS and maintain comfort levels while undertaking different activities, for example walking, running, or sitting. In a further integrated variation of this embodiment, the rotary actuator accepts instructions directly from the smart phone via a wired or wireless communication link (not shown).

A further variation of the embodiment depicted in FIG. 14 includes the substitution of photometric oximeters (not shown) for the pressure sensors 1403 mounted on the inner surfaces 7 of the paddles 5. The oximeter sensor output is sent electronically over a wire communication link 1409 embedded in the paddles and further connected through the paddle connectors 6 to a controller 1402 mounted in the adapter 1. The controller is coupled with a digital transmitter to send a control signal via a wireless communication link with the smart phone 1418 to display detected oxygen levels 1419. In a further variation to this embodiment, the smart phone is further programmed to provide an audible warning when oxygen levels fall below a minimum level stored in the smart phone memory.

While the embodiments disclosed above have application in the field of prosthetics, in orthotic or orthopedic support device embodiments, it is to be appreciated that the lost motion capture and adjustability principles of the invention can be applied using RAS paddles to control motion of bone across a fracture or bones sharing a common joint, as depicted in FIG. 20, to immobilize such fractures or joints or to support joints in order to promote healing or correction, while allowing compression forces to be varied over time or from time to time for therapeutic benefit, comfort, or for particular activities that may require more or less immobilization or support.

It is also to be appreciated that the principals of the invention can be applied to exoskeletal embodiments, such as depicted in FIG. 21, where the user is, for example, not an amputee, but requires a socket device that captures lost motion of the underlying skeletal structure to which the socket attaches in order, for example, to immobilize a joint, increase the load bearing strength of skeletal structures, or increase the association between the physical movement of the skeletal structure and the resulting movement of the RAS. A further advantage of the RAS system in exoskeletal applications is that it allows user adjustments in the field and the RAS can be adjusted to fit different users who may need to use the exoskeletal application at different times.

It will be apparent to those skilled in the art that changes and modifications may be made in the embodiments illustrated and described, without departing from the spirit and the scope of the invention. Thus, the invention is not to be limited to the particular forms herein shown and described except insofar as indicated by the scope of the appended claim.

What is claimed is:

1. A system for engaging a target with a prosthetic device comprising:
   a first paddle having an inner surface and an outer surface;
   a second paddle having an inner surface,
   wherein each paddle has a first paddle end and a second paddle end,
   wherein each of the first paddle ends lies on an opposite end of each paddle from each of the second paddle ends;
   an adapter,
   wherein the adapter further comprises:
   a connector assembly; and
   a prosthetic attachment interface,
   wherein the connector assembly attaches the prosthetic attachment interface to the first paddle ends of each of the first and second paddles,
   wherein the first paddle, the second paddle, and the adapter form a socket with the adapter at the socket distal end and the second paddle ends of each paddle at the socket proximal end,
   wherein the socket is adapted to substantially support the target during a weight-bearing user activity,
   wherein the prosthetic attachment interface is adapted to connect to a proximal end of the prosthetic device,
   wherein the socket has a center axis,
   wherein the paddles are chosen from a plurality of paddles of different shapes in such a way that the inner surface of the first paddle is substantially coextensive with a first target area and the inner surface of a second paddle is substantially coextensive with a second target area,
   wherein the inner surface of the first paddle is adapted to be in contact with the first target area and the inner surface of the second paddle is adapted to be in contact with the second target area when worn; and
   an external tool comprising:
   a projectable member rigidly affixed to a compression bar, and the compression bar is rigidly affixed to the first paddle, such that moving the projectable member inwardly and outwardly from the center axis moves the compression bar and the first paddle inwardly and outwardly to press the inner surface of the first paddle against the first target area to impart an optimal tissue compression to the first target area,
   wherein the connector assembly is adapted to maintain the optimal tissue compression on the first target area when the compression bar is detached from the first paddle,
   wherein the connector assembly is adapted to press together the inner surface of the second paddle and the second target area in such a way that the inner surface of the second paddle imparts an optimal tissue compression to the second target area,
   wherein the first paddle is made of a first material and the second paddle is made of a second material and the first material and second material are sufficiently stiff to impart the optimal tissue compression to the target areas,
   wherein the connector assembly is adapted to impart substantially no compression to nonpaddle areas when worn,
   wherein the adapter is adapted to be worn during normal ambulation,
   wherein the nonpaddle areas include relief areas.

2. The system of claim 1, wherein the connector assembly further comprises:
   a cam follower; and
   a cam,
   wherein the cam follower and cam are operatively connected to move the outer surface towards the center axis and adapted to press together the inner surface of the first paddle and the first target area in such a way that the inner surface of the first paddle imparts the optimal tissue compression to the first target area.

3. The system of claim 2, further comprising
   a slidable coupling track connected to the first paddle end of the first paddle,
   wherein the connector assembly further comprises:
   a paddle mount leadscrew nut;
   a macro adjustment fastener adapted to adjustably affix the slidable coupling track to the paddle mount leadscrew nut for selecting an initial compression on the first target area; and
   a fine adjustment leadscrew fixably attached to the paddle mount leadscrew nut and adapted to impart the optimal tissue compression to the first target area.

4. The system of claim 3, further comprising:
   a stabilizer band,
   wherein the stabilizer band is attached across a portion of the first paddle at approximately the second paddle end.

5. The system of claim 4, wherein the system further comprises the prosthetic device attached to the prosthetic attachment interface at the proximal end of the prosthetic device.

6. The system of claim 5, wherein the first paddle is a flared paddle.

7. The system of claim 4,
   wherein the stabilizer band is a stabilizer cuff,
   wherein the system further comprises:
   a pump; and
   a tube connecting the pump to the stabilizer cuff,
   wherein the controller outputs a cuff control signal to the pump via the communication link,
   wherein the pump generates a pressure of the stabilizer cuff via the tube as a function of the cuff control signal
   wherein the stabilizer cuff is operable to stiffen as a function of the pressure of the stabilizer cuff.

8. The system of claim 1, wherein the connector assembly attaches the prosthetic attachment interface to the first paddle end of the first paddle through a rotatable connector, wherein the rotatable connector is operable to rotate the first paddle towards the center axis in such a way as to impart the optimal tissue compression to the first target area.

9. The system of claim 1, wherein the external tool further comprises:
   a controller; and
   a communication link,
   wherein the projectable member further comprises an actuator,
   wherein the controller outputs a control signal to the actuator via the communication link to operate the projectable member in such a way as to move the compression bar inwardly or outwardly from the center axis.

10. The system of claim 1 wherein the external tool further comprises:
a sensor;
a controller memory; and
an expected sensor value associated with the optimal tissue compression to the first target area,
wherein the expected sensor value associated with the optimal tissue compression to the first target area is stored in the controller memory,
wherein the sensor sends a sensor output to the controller via the communication link,
wherein the controller determines a difference between the sensor output and the expected sensor value associated with the optimal tissue compression to the first target area,
wherein the controller modifies the control signal as a function of the difference between the sensor output and the expected sensor value associated with the optimal tissue compression to the first target area.

11. The system of claim 1, wherein the system further comprises:
a liner;
a magnet attached to the liner;
a magnetic field sensor; and
a display,
wherein the magnetic field sensor is attached to the first paddle,
wherein the liner is adapted to be worn over the first target area and the nonpaddle areas in such a way that the magnet aligns with a physical feature of the target,
wherein selection of the magnet strength, the magnetic field sensor sensitivity, the physical feature, and the magnet location on the liner is coordinated in such a way that the magnetic field sensor outputs a display signal to the display only when the inner surface of the first paddle is substantially aligned with the first target area.

12. A system for engaging a target with a prosthetic device comprising:
a plurality of paddles, each paddle having an inner surface, an outer surface, a first paddle end, and a second paddle end,
wherein the first paddle end and second paddle end lie on opposite ends of the paddle;
an adapter;
a slidable coupling track attached to the first paddle end,
wherein the adapter further comprises:
a connector assembly; and
a prosthetic attachment interface,
an external tool comprising a projectable member rigidly affixed to a compression bar,
wherein the compression bar is rigidly affixed to the paddle such that moving the projectable member inwardly and outwardly from the center axis moves the compression bar and the paddle inwardly and outwardly to press the inner surface of the paddle against a target area to impart an optimal tissue compression to the target area;
wherein the connector assembly adjustably attaches the prosthetic attachment interface to the slidable coupling track,
wherein the plurality of paddles and the adapter form a socket with the adapter at the socket distal end and the second paddle end at the socket proximal end,
wherein the socket is adapted to substantially support the target during a weight bearing user activity,
wherein the prosthetic attachment interface is adapted to connect to a proximal end of the prosthetic device,
wherein the socket has a center axis,
wherein the plurality of paddles are chosen from a larger plurality of paddles of different shapes in such a way that the inner surface of each chosen paddle is substantially coextensive with a target area,
wherein the inner surface is adapted to be in contact with the target area when worn,
wherein the slidable coupling track is configured to allow movement of the connector assembly along the slidable coupling track radially with respect to the center axis to press together the inner surface and the target area in such a way that the outer surface moves towards the center axis and the inner surface imparts an optimal tissue compression to the target area,
wherein the paddle is made of a material that is sufficiently stiff to impart the optimal tissue compression to the target area,
wherein the connector assembly is adapted to impart substantially no compression to a nonpaddle area when worn,
wherein the adapter is adapted to be worn during normal ambulation,
wherein the nonpaddle area is configured to include a relief area.

13. The system of claim 12, wherein the connector assembly further comprises:
a cam follower;
a cam;
a paddle mount leadscrew nut;
a macro adjustment fastener adapted to adjustably affix the slidable coupling track to the paddle mount leadscrew nut for selecting an initial compression on the target area; and
a fine adjustment leadscrew fixably attached to the paddle mount leadscrew nut and adapted to impart the optimal tissue compression to the target area.

14. The system of claim 13, wherein the system further comprises:
a second paddle having an inner surface, an outer surface, a first paddle end, and a second paddle end; and
a stabilizer band,
wherein the connector assembly attaches the prosthetic attachment interface to the first paddle end of the second paddle,
wherein the paddle, the second paddle, and the adapter form the socket with the adapter at the socket distal end and the second paddle ends of each paddle at the socket proximal end,
wherein the second paddle is chosen from the plurality of paddles of different shapes in such a way that the inner surface of the second paddle is substantially coextensive with a second target area,
wherein the stabilizer band is coupled to a portion of at least two of the paddles at approximately the second paddle end,
wherein the number of relief areas equals the number of paddles.

15. The system of claim 12, wherein the connector assembly further comprises:
an adjustment fastener adapted to adjustably affix the slidable coupling track to the prosthetic attachment interface;
a second paddle having an inner surface, an outer surface, a first paddle end, and a second paddle end; and
a stabilizer band, wherein the connector assembly attaches the prosthetic attachment interface to the first paddle end of the second paddle, wherein the paddle, the second paddle, and the adapter form the socket with the adapter at the socket distal end and the second paddle ends of each paddle at the socket proximal end, wherein the second paddle is chosen from a plurality of paddles of different shapes in such a way that the inner surface of the second paddle is substantially coextensive with a second target area, wherein the stabilizer band is attached to a portion of at least two of the paddles at approximately the second paddle end, wherein the number of relief areas equals the number of paddles.

16. The system of claim 12, wherein the system further comprises:

a second paddle having an inner surface, an outer surface, a first paddle end, and a second paddle end, wherein the connector assembly attaches the prosthetic attachment interface to the first paddle end of the second paddle, wherein the paddle, the second paddle, and the adapter form the socket with the adapter at the socket distal end and the second paddle ends of each paddle at the socket proximal end, wherein the second paddle is chosen from a plurality of paddles of different shapes in such a way that the inner surface of the second paddle is substantially coextensive with a second target area, wherein the number of relief areas equals the number of paddles.

* * * * *